United States Patent
Du et al.

(10) Patent No.: US 9,339,284 B2
(45) Date of Patent: May 17, 2016

(54) SYSTEMS AND METHODS FOR CONTROLLING DELIVERY OF ULTRASONIC ENERGY TO A BODILY TISSUE

(71) Applicant: Med-Sonics Corporation, Erie, PA (US)

(72) Inventors: Shu Du, Erie, PA (US); Tao Song, Erie, PA (US)

(73) Assignee: Med-Sonics Corporation, Erie, PA (US)

( * ) Notice: Subject to any disclaimer, the term of this patent is extended or adjusted under 35 U.S.C. 154(b) by 539 days.

(21) Appl. No.: 13/669,942

(22) Filed: Nov. 6, 2012

(65) Prior Publication Data

US 2014/0128863 A1    May 8, 2014

(51) Int. Cl.
*A61B 17/22*    (2006.01)
*A61N 7/00*    (2006.01)
*A61B 17/00*    (2006.01)

(52) U.S. Cl.
CPC . *A61B 17/22012* (2013.01); *A61B 2017/00137* (2013.01); *A61B 2017/00146* (2013.01); *A61B 2017/22014* (2013.01); *A61N 2007/0073* (2013.01)

(58) Field of Classification Search
CPC .............. A61B 17/22012; A61B 2017/00137; A61B 2017/00146; A61B 2017/22014; A61N 2007/0073
See application file for complete search history.

(56) References Cited

U.S. PATENT DOCUMENTS

| | | | |
|---|---|---|---|
| 3,433,226 A | 3/1969 | Boyd | |
| 3,872,472 A | 3/1975 | Moschgat | |
| 3,893,106 A | 7/1975 | Schulein | |
| 4,169,984 A | 10/1979 | Parisi | |
| 4,474,180 A | 10/1984 | Angulo | |
| 4,660,573 A | 4/1987 | Brumbach | |
| 4,886,491 A | 12/1989 | Parisi et al. | |
| 4,920,954 A | 5/1990 | Alliger et al. | |
| 4,933,918 A | 6/1990 | Landsrath et al. | |
| 5,358,505 A | 10/1994 | Wuchinich | |
| 5,397,301 A | 3/1995 | Pflueger et al. | |
| 5,427,118 A | 6/1995 | Nita et al. | |
| 5,447,509 A | 9/1995 | Mills et al. | |

(Continued)

FOREIGN PATENT DOCUMENTS

EP    1025806 B1    4/2006
WO    WO 99/44514 A1    9/1999

(Continued)

OTHER PUBLICATIONS

International Search Report and Written Opinion for International Application No. PCT/US2013/064990, mailed Mar. 6, 2014.

(Continued)

*Primary Examiner* — Rex R Holmes

(57) ABSTRACT

An apparatus includes a generator including a control module that is operably coupled to a power module. The power module is configured to produce an electronic signal to be received by an ultrasonic energy delivery assembly. The ultrasonic energy delivery assembly is characterized by a natural frequency, and the electronic signal is characterized by a frequency. The control module is configured to send a control signal to the power module to randomly vary the frequency of the electronic signal within a range defined at least in part by the natural frequency.

21 Claims, 13 Drawing Sheets

(56) References Cited

U.S. PATENT DOCUMENTS

| | | |
|---|---|---|
| 5,527,273 A | 6/1996 | Manna et al. |
| 5,540,656 A | 7/1996 | Pflueger et al. |
| 5,562,609 A | 10/1996 | Brumbach |
| 5,630,837 A | 5/1997 | Crowley |
| 5,674,235 A | 10/1997 | Parisi |
| 5,720,710 A | 2/1998 | Tachibana et al. |
| 5,735,280 A | 4/1998 | Sherman et al. |
| 5,827,201 A | 10/1998 | Samson et al. |
| 5,897,569 A | 4/1999 | Kellogg et al. |
| 5,989,275 A | 11/1999 | Estabrook et al. |
| 6,050,971 A | 4/2000 | Garnier |
| 6,063,098 A | 5/2000 | Houser et al. |
| 6,071,260 A | 6/2000 | Halverson |
| 6,093,150 A | 7/2000 | Chandler et al. |
| 6,165,163 A | 12/2000 | Chien et al. |
| 6,217,543 B1 | 4/2001 | Anis et al. |
| 6,274,963 B1 | 8/2001 | Estabrook et al. |
| 6,296,620 B1 | 10/2001 | Gesswein et al. |
| 6,299,591 B1 | 10/2001 | Banko |
| 6,383,183 B1 | 5/2002 | Sekino et al. |
| 6,450,975 B1 | 9/2002 | Brennan et al. |
| 6,508,781 B1 | 1/2003 | Brennan et al. |
| 6,511,478 B1 | 1/2003 | Burnside et al. |
| 6,514,220 B2 | 2/2003 | Melton, Jr. et al. |
| 6,524,299 B1 | 2/2003 | Tran et al. |
| 6,577,042 B2 | 6/2003 | Lee et al. |
| 6,623,444 B2 | 9/2003 | Babaev |
| 6,743,239 B1 | 6/2004 | Kuehn et al. |
| 6,819,027 B2 | 11/2004 | Saraf |
| 6,866,670 B2 | 3/2005 | Rabiner et al. |
| 6,942,677 B2 | 9/2005 | Nita et al. |
| 7,089,063 B2 | 8/2006 | Lesh et al. |
| 7,204,820 B2 | 4/2007 | Akahoshi |
| 7,335,169 B2 | 2/2008 | Thompson et al. |
| 7,335,180 B2 | 2/2008 | Nita et al. |
| 7,371,235 B2 | 5/2008 | Thompson et al. |
| 7,431,728 B2 | 10/2008 | Gerry et al. |
| 7,494,467 B2 | 2/2009 | Makin et al. |
| 7,494,468 B2 | 2/2009 | Rabiner et al. |
| 7,503,895 B2 | 3/2009 | Rabiner et al. |
| 7,682,366 B2 | 3/2010 | Sakurai et al. |
| 7,955,293 B2 | 6/2011 | Nita et al. |
| 8,052,607 B2 | 11/2011 | Byrd |
| 8,062,566 B2 | 11/2011 | Nita et al. |
| 8,115,366 B2 | 2/2012 | Hoffman et al. |
| 8,133,236 B2 | 3/2012 | Nita |
| 8,152,753 B2 | 4/2012 | Nita et al. |
| 8,182,467 B2 | 5/2012 | Nguyen et al. |
| 8,221,343 B2 | 7/2012 | Nita et al. |
| 8,246,643 B2 | 8/2012 | Nita |
| 8,308,677 B2 | 11/2012 | Nita et al. |
| 8,721,581 B2 | 5/2014 | Zolli |
| 9,173,667 B2 | 11/2015 | Du et al. |
| 2003/0212333 A1 | 11/2003 | Rabiner et al. |
| 2004/0127925 A1 | 7/2004 | Du et al. |
| 2006/0004396 A1 | 1/2006 | Easley et al. |
| 2006/0090956 A1 | 5/2006 | Peshknvskiy et al. |
| 2006/0116610 A1* | 6/2006 | Hare et al. .................. 601/2 |
| 2008/0171965 A1 | 7/2008 | Soltani et al. |
| 2008/0294051 A1 | 11/2008 | Koshigoe et al. |
| 2009/0018472 A1 | 1/2009 | Soltani et al. |
| 2010/0274269 A1 | 10/2010 | Song et al. |
| 2010/0331871 A1 | 12/2010 | Nield et al. |
| 2011/0015631 A1 | 1/2011 | Weiner et al. |
| 2011/0213397 A1 | 9/2011 | Mathonnet |
| 2011/0301506 A1 | 12/2011 | Volz |
| 2012/0016272 A1 | 1/2012 | Nita et al. |
| 2012/0157890 A1 | 6/2012 | Govari et al. |
| 2012/0163126 A1 | 6/2012 | Campbell et al. |
| 2012/0191115 A1 | 7/2012 | Gilbert |
| 2012/0209303 A1 | 8/2012 | Frankhouser et al. |
| 2012/0232435 A1 | 9/2012 | Nita et al. |
| 2013/0253387 A1* | 9/2013 | Bonutti et al. .................. 601/46 |
| 2014/0107534 A1 | 4/2014 | Du et al. |
| 2014/0364775 A1 | 12/2014 | Du et al. |

FOREIGN PATENT DOCUMENTS

| | | |
|---|---|---|
| WO | WO 2005/072391 A2 | 8/2005 |
| WO | WO 2006/059966 A1 | 6/2006 |
| WO | WO 2012/118018 A1 | 9/2012 |

OTHER PUBLICATIONS

"Design Considerations in Small-Diameter Medical Tubing," [online] [Retrieved from the Internet] Retrieved from http://www.mddio9nline.com/print/181, Retrieved on Sep. 21, 2012.

Cyberwand™, Dual Probe Ultrasonic Lithotripter System, Cybersonics, Inc.

"Fundamentals of Ultrasonic Imaging and Flaw Detection," National Instruments tutorial, Feb. 11, 2010.

"Pebax® Tubing Grades," Applied Medical Tubing [online] [Retrieved from the Internet] Retrieved on www.appliedtubing.com/_mgxroot/page_10795.html, Retrieved on Nov. 1, 2012.

Pagnani, C. et al., "Prevention of stone migration with the Accordion during endoscopic ureteral lithotripsy," J Endourology, 26(5):484-488 (May 2012).

* cited by examiner

600

```
┌─────────────────────────────────┐
│ Receive a first feedback signal │
│ associated with a nominal       │
│ component of an electronic      │
│ signal conveyed to an ultrasonic│
│ energy delivery assembly        │
│ characterized by a natural      │
│ frequency.                      │
│ 602                             │
└─────────────────────────────────┘
              │
              ▼
┌─────────────────────────────────┐
│ Determine the natural frequency │
│ of the ultrasonic energy        │
│ delivery assembly based at      │
│ least in part on the first      │
│ feedback signal.                │
│ 604                             │
└─────────────────────────────────┘
              │
              ▼
┌─────────────────────────────────┐
│ Receive a second feedback signal│
│ associated with a noise         │
│ component of the electronic     │
│ signal.                         │
│ 606                             │
└─────────────────────────────────┘
              │
              ▼
┌─────────────────────────────────┐
│ Send a control signal based at  │
│ least in part on the second     │
│ feedback signal to vary the     │
│ frequency of the electronic     │
│ signal.                         │
│ 608                             │
└─────────────────────────────────┘
```

```
┌─────────────────────────────────────┐
│ Send an electronic signal to be     │
│ received by an ultrasonic energy    │
│ delivery assembly.                  │
│ 702                                 │
└─────────────────────────────────────┘
                  │
                  ▼
┌─────────────────────────────────────┐
│ Receive a control signal based at   │
│ least in part on a random value.    │
│ 704                                 │
└─────────────────────────────────────┘
                  │
                  ▼
┌─────────────────────────────────────┐
│ Vary the frequency of the electronic│
│ signal within a range defined at    │
│ least in part by the natural        │
│ frequency of the ultrasonic energy  │
│ delivery assembly in response to    │
│ receiving the control signal.       │
│ 706                                 │
└─────────────────────────────────────┘
```

FIG. 14

SYSTEMS AND METHODS FOR CONTROLLING DELIVERY OF ULTRASONIC ENERGY TO A BODILY TISSUE

BACKGROUND

The embodiments described herein relate generally to a systems and methods used in conjunction with an ultrasonic ablation device and, more specifically, to systems and methods of controlling the delivery of ultrasonic energy to a bodily tissue via a transmission member (e.g., a catheter, a probe or the like).

Known ultrasonic energy transmission systems are used in many different medical applications, such as, for example, in medical imaging, to disrupt obstructions and/or ablate bodily tissue. In known ultrasonic energy transmission systems for tissue ablation, ultrasonic energy is transferred from an ultrasonic energy source through a transducer horn and then a transmission member, such as a wire, to a distal head. Ultrasonic energy propagates through the transmission member as a periodic wave thereby causing the distal head to vibrate. Such vibrational energy can be used to ablate or otherwise disrupt bodily tissue, for example, a vascular obstruction, a kidney stone or the like. To effectively reach various sites for treatment of intravascular occlusions or regions within the urinary tract, such ultrasonic transmission members are often constructed from a thin, flexible material, and have lengths of about 65 cm or longer.

Known ultrasonic energy transmission systems include a generator, a transducer assembly and a probe (or transmission member). The generator is configured to generate, control, amplify, and/or transfer an alternating electronic signal of a desired frequency (e.g., a voltage signal) to the transducer assembly. The transducer assembly typically contains one or more piezoelectric crystals, which, when excited by the high frequency electronic signal, expand and contract at high frequency. These high-frequency vibrations are amplified by the ultrasonic horn into the ultrasonic energy that is transmitted to a probe (or transmission member). The ultrasonic energy is transmitted to the distal end of the probe to ablate and/or otherwise disrupt a bodily tissue.

Because known probes are often traversed through tortuous anatomic structures to reach the site of treatment, transmission members are often constructed to be elastic and/or flexible, but also with sufficient strength to transmit ultrasonic energy to the distal tip (e.g., to ablate vascular or urinary obstructions). To find a balance between strength and flexibility, some known transmission members are tapered such that the diameter of the distal end portion decreases, thereby providing a transmission member having greater flexibility. For example, some known transmission members have a diameter at the proximal end that is greater than a diameter at a distal end. Moreover, some known transmission members can include a distal tip or "head" that is welded to the reduced diameter section and is positioned adjacent the tissue to be treated.

To maximize energy transmission to the target bodily tissue, known systems are often configured to produce ultrasonic energy having a frequency that matches the natural frequency of the energy delivery assembly (i.e., the transducer and/or probe assembly). When operating at the natural frequency (i.e., at resonance conditions), the amplitude of the ultrasonic energy wave (or signal) travelling through the transmission member is at its maximum. The transmission member can be thought of as having a standing wave of ultrasonic energy traveling along its length. More particularly, the standing wave produces a series of nodes (regions of minimum displacement) and anti-nodes (regions of maximum displacement) along the length of the transmission member. Thus, when operating in resonance conditions, the displacement and/or vibration at the anti-nodes are at a maximum for a given power level. Each of the anti-nodes can produce cavitations in fluids in contact with the transmission member to cause the destruction of the adjacent tissue.

Some known systems include algorithms to tune the frequency of the electronic signal (sent from the generator to the transducer) to more closely match the natural frequency of the energy delivery assembly. For example, in some known systems, the amplitude and/or frequency of the ultrasonic energy can be controlled by monitoring the current input (or electronic signal input) to the transducer assembly, and varying the power input to the transducer assembly to maintain the electrical current input to the transducer assembly at a constant level. Such known algorithms can be used to account for variations in the natural frequency of the transmission member due to part-to-part variation, and the conditions in which the energy delivery assembly is used, and the like.

Operating a known ultrasonic transmission member continuously at its natural frequency, however, can reduce the reliability of the transmission member. More particularly, operation at a single frequency produces standing waves in the transmission member that are substantially constant. Similarly stated, when operating at a constant frequency, the location of the vibration anti-nodes within the transmission member remains substantially constant. Thus, the continued application of high stress to such regions increases the likelihood of mechanical failure. Moreover, operation at a constant frequency, even at resonance, may not effectively ablate the target bodily tissue.

Thus, a need exists for an improved systems and methods of controlling the delivery of ultrasonic energy to a bodily tissue.

SUMMARY

Systems and methods for transmitting ultrasonic energy for use with an ultrasonic ablation system are described herein. In some embodiments, an apparatus includes a generator including a control module that is operably coupled to a power module. The power module is configured to produce an electronic signal to be received by an ultrasonic energy delivery assembly. The ultrasonic energy delivery assembly is characterized by a natural frequency, and the electronic signal is characterized by a frequency. The control module is configured to send a control signal to the power module to randomly vary the frequency of the electronic signal within a range defined at least in part by the natural frequency.

BRIEF DESCRIPTION OF THE DRAWINGS

FIG. 13 is a flowchart illustrating a method of receiving a first and a second feedback signal and sending a control signal based in part on the feedback signals to vary the frequency of an electronic signal, according to an embodiment.

FIG. 14 is a flowchart illustrating a method of sending an electronic signal characterized by a frequency in response to receiving a control signal based in part on a random value, according to an embodiment.

DETAILED DESCRIPTION

Figure 1:
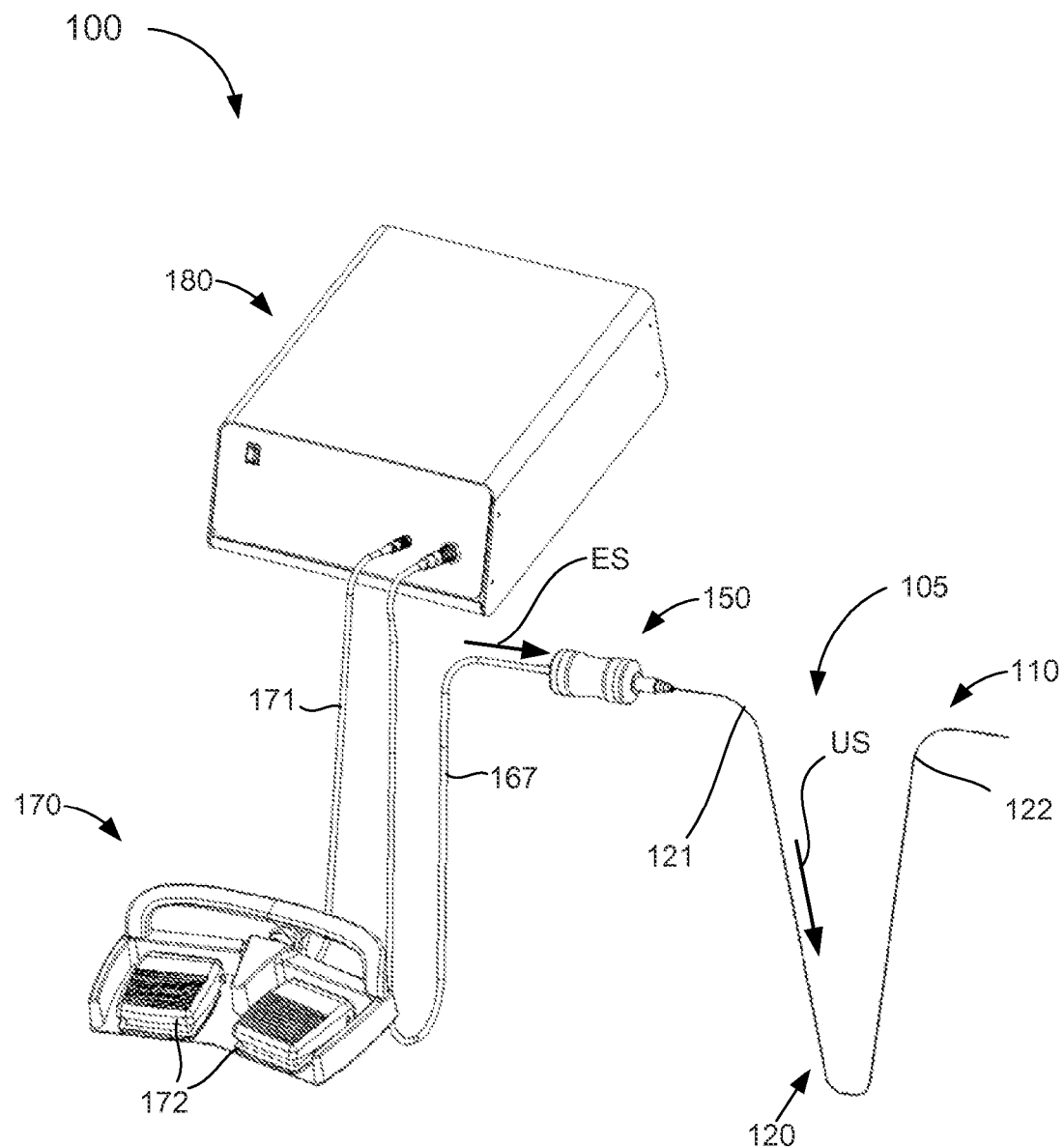
FIG. 1 is an illustration of a system for delivering ultrasonic energy to a bodily tissue according to an embodiment.

Systems and methods for transmitting ultrasonic energy for use with an ultrasonic ablation system are described herein. In some embodiments, an apparatus includes a generator including a control module that is operably coupled to a power module. The power module is configured to produce an electronic signal to be received by an ultrasonic energy delivery assembly. The ultrasonic energy delivery assembly is characterized by a natural frequency, and the electronic signal is characterized by a frequency. The control module is configured to send the control signal to the power module to randomly vary the frequency of the electronic signal within a range defined at least in part by the natural frequency.

In some embodiments, an apparatus includes a generator including a control module and a feedback module that is operatively coupled to the control module. The generator is operably coupled to a power module configured to produce an electronic signal to be received by an ultrasonic energy delivery assembly that is characterized by a natural frequency. The electronic signal is characterized by a frequency. The feedback module is configured to produce a feedback signal and a noise signal. The feedback signal is associated with a nominal component of the electronic signal produced by the power module, and the noise signal is based at least in part on a noise component of the electronic signal produced by the power module. The control module is configured to determine the natural frequency based on the feedback signal. The control module is also configured to send a control signal that is based at least in part on the noise signal, to the power module to vary the frequency of the electronic signal within a range defined at least in part by the natural frequency.

In some embodiments, a method includes sending an electronic signal to be received by an ultrasonic energy delivery assembly characterized by a natural frequency. The electronic signal is characterized by a frequency. The method also includes producing a control signal to randomly vary the frequency of the electronic signal within a range defined at least in part by the natural frequency. The frequency of the electronic signal is varied in response to the control signal.

In some embodiments, a method includes receiving a first feedback signal associated with a nominal component of an electronic signal conveyed to an ultrasonic energy delivery assembly. The ultrasonic energy delivery assembly is characterized by a natural frequency. The method includes determining the natural frequency of the ultrasonic energy delivery assembly based at least in part on the first feedback signal. A second feedback signal associated with a noise component of the electronic signal is received. The method further includes producing a control signal, based at least in part on the second feedback signal, and sending the control signal to vary a frequency of the electronic signal.

In some embodiments, a system includes a transmission member, an ultrasonic transducer and a generator. The transmission member is configured to convey an ultrasonic energy signal to a target tissue. The ultrasonic transducer is configured to receive an electronic signal and produce the ultrasonic energy signal in response to the electronic signal. The ultrasonic transducer is configured to convey the ultrasonic energy signal to the transmission member. The generator is configured to produce the electronic signal. The generator, ultrasonic transducer and/or the transmission member are collectively configured such that when the ultrasonic energy signal is conveyed via the transmission member, a resulting vibrational anti-node of the transmission member is randomly varied along the longitudinal axis of the transmission member.

In some embodiments, a method includes sending an electronic signal to be received by an ultrasonic energy delivery assembly characterized by a natural frequency. The electronic signal is characterized by a frequency. A control signal, which is based at least in part on a random value, is received from a control module. The frequency of the electronic signal is varied within a range defined at least in part by the natural frequency in response to receiving the control signal.

As used in this specification, the terms "proximal" and "distal" refer to the direction closer to and away from, respectively, a user who would place the device into contact with a patient. Thus, for example, the end of a device first touching the body of the patient would be the distal end, while the opposite end of the device (e.g., the end of the device being manipulated by the user) would be the proximal end of the device.

As used herein, the terms "about" and "approximately" generally mean plus or minus 10% of the value stated. For example, about 0.5 would include 0.45 and 0.55, about 10 would include 9 to 11, about 1000 would include 900 to 1100.

As used herein, the term "target tissue" refers to an internal or external tissue of or within a patient to which ultrasonic energy ablation techniques are applied. For example, a target tissue can be cancer cells, tumor cells, lesions, vascular occlusions, thrombosis, calculi, uterine fibroids, bone metastases, adenomyosis, or any other bodily tissue. Furthermore, the presented examples, of target tissues are not an exhaustive list of suitable target tissues. Thus, the ultrasonic energy systems described herein are not limited to the treatment of the aforementioned tissues and can be used on any suitable bodily tissue. Moreover, a "target tissue" can also include an artificial substance within or associated with a body, such as for example, a stent, a portion of an artificial tube, a fastener within the body or the like. Thus, for example, the ultrasonic energy systems described herein can be used on or within a stent or artificial bypass graft.

Embodiments described herein relate to ultrasonic energy ablation systems and methods for controlling the delivery of ultrasonic energy using such systems. In such systems, a transmission member can be operably coupled to an ultrasonic energy source to deliver ultrasonic energy to a target bodily tissue. For example, FIG. 1 is an illustration of an ultrasonic energy ablation system 100, according to an embodiment. The ultrasonic energy ablation system 100 (also referred to herein as "ultrasonic system" or simply "system") includes an ultrasonic generator 180, a foot switch 170 and an ultrasonic energy delivery assembly 105 (which includes an ultrasonic transducer assembly 150, and a probe assembly 110). As described in detail herein, the ultrasonic generator 180 (or "generator") is configured to generate, control, amplify, and/or transfer an electronic signal ES (e.g., a voltage or current) to the transducer assembly 150. The ultrasonic generator 180 can be any of the generators described herein, and can be operated according to any of the methods described herein.

As shown in FIG. 1, the foot switch 170 is in electric communication with the ultrasonic generator 180 via a foot switch cable 171. The foot switch 170 includes a set of pedals 172 (e.g., two pedals as shown) that are operative in controlling the delivery of the ultrasonic electrical energy ES supplied to the ultrasonic transducer assembly 150. For example, in some embodiments, a user (e.g., a physician, technician, etc.) can engage and/or depress one or more of the pedals 172 to control the ultrasonic electrical energy ES supplied to the ultrasonic transducer assembly 150 such that, in turn, the probe assembly 110 delivers the desired ultrasonic energy US to the bodily tissue, as further described in detail herein.

Figure 2:
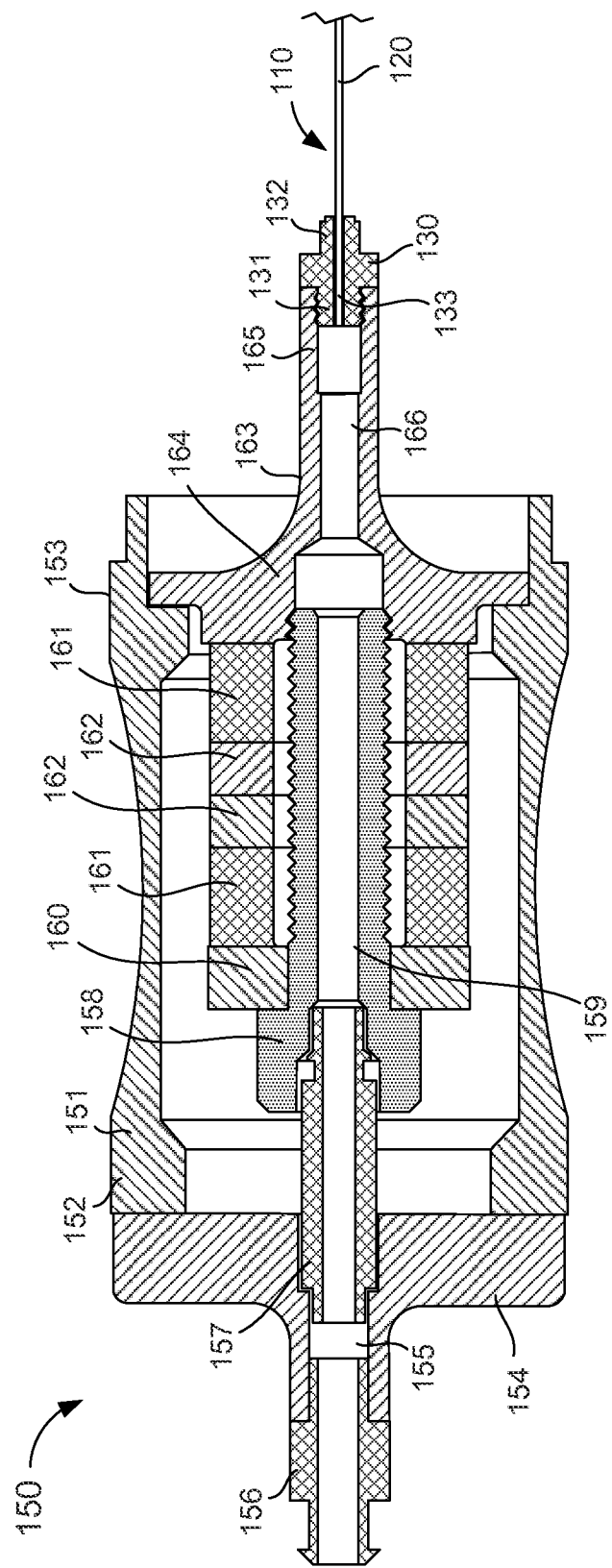
FIG. 2 is a cross-sectional view of the ultrasonic transducer assembly shown in the system of FIG. 1.

The transducer assembly 150 is in electric communication with the ultrasonic generator 180 via a transducer cable 167. In this manner, the transducer assembly 150 can receive the electrical signal ES (i.e., voltage and/or current) from the ultrasonic generator 180. The transducer assembly 150 is configured to produce and amplify the ultrasonic energy via a set of piezoelectric members 162 (i.e., piezoelectric rings as shown in FIG. 2) and an ultrasonic horn 163 (also shown in FIG. 2), and transfer the ultrasonic energy US to the probe assembly 110 and/or the transmission member 120. The transducer assembly 150 can be any suitable assembly of the types shown and described herein. The ultrasonic horn 163 can be used as an amplification unit to amplify and efficiently transfer the acoustic energy from the ultrasonic transducer into the treated media, which, for many biomedical applications is a liquid.

In some embodiments, as shown in FIG. 2, the transducer assembly 150 includes a housing 151 having a proximal end portion 152 and a distal end portion 153. The housing 151 is configured to house or otherwise enclose at least a portion of a flow tube 157, a bolt 158, a back plate 160, a set of insulators 161, a set of piezoelectric rings 162, and a transducer horn 163.

The proximal end portion 152 of the housing 151 is coupled to a proximal cover 154 (e.g., via an adhesive, a press or friction fit, a threaded coupling, a mechanical fastener, or the like). The proximal cover 154 defines an opening 155 such that the proximal cover 154 can receive a portion of a connector 156 (e.g., a luer connector) on a proximal side thereof (e.g., substantially outside the housing 151) and a portion of the flow tube 157 on a distal side thereof (e.g., substantially inside the housing 151). Expanding further, the proximal cover 154 can receive the connector 156 and the flow tube 157 such that the proximal cover 154 forms a substantially fluid tight seal with the connector 156 and the flow tube 157. In this manner, a vacuum can be applied via the connector 156 to irrigate and/or aspirate the region of the body within which the probe assembly 110 is disposed. Similarly stated, this arrangement results in the connector 156 being placed in fluid communication with the lumen 122 defined by the transmission member 120.

The distal end portion 153 of the housing 151 is configured to receive the transducer horn 163 such that the transducer horn 163 is coupled to an inner surface of the housing 151. More specifically, the transducer horn 163 can be disposed at least partially within the housing 151 such that the transducer horn 163 can be moved relative to the housing 151 (e.g., when amplifying the ultrasonic energy), but not moved out of the housing 151 during normal use. The transducer horn 163 includes a proximal end portion 164 and a distal end portion 165 and defines a lumen 166 therethrough. The lumen 166 is configured to receive a portion of the bolt 158 at the proximal end portion 164 of the transducer horn 163 and a portion of the probe assembly 120 at the distal end portion 165 of the transducer horn 163, both of which are described in further detail herein.

As shown in FIG. 2, the back plate 160, the insulators 161, and the piezoelectric rings 162 are disposed within the housing 151 and about the bolt 158. More specifically, the arrangement of the back plate 160, the insulators 161, and the piezoelectric rings 162 is such that the back plate 160 is disposed proximal to the insulators 161 and the piezoelectric rings 162. The piezoelectric rings 162 are each disposed between the insulators 161. Similarly stated, a first insulator 161 is disposed proximal to the piezoelectric rings 162 and a second insulator 161 is disposed distal to the piezoelectric rings 162. The piezoelectric rings 162 are in electric communication (e.g., via wires not shown in FIGS. 1 and 2) with the ultrasonic generator 180, as described in further detail herein.

As shown in FIG. 2, a portion of the bolt 158 is configured to be disposed within the lumen 166 defined by the transducer horn 163. More specifically, the portion of the bolt 158 forms a threaded fit with an inner surface of the transducer horn 163 that defines the lumen 166. In this manner, the bolt 158 can be advanced within the lumen 166 such that the bolt 158 exerts a compressive force on the backing plate 160, the insulators 161, and the piezoelectric rings 162. Thus, the backing plate 160, the insulators 161, and the piezoelectric rings 162 are retained between a head of the bolt 158 (e.g., at the proximal end) and a proximal surface of the transducer horn 163. The torque applied to the bolt and/or the clamping force exerted between the head of the bolt 158 and the proximal surface of the transducer horn 163 is such that that the deviation of the transducer natural frequency deviation is within ten percent from nominal. Therefore, in use, the piezoelectric rings 162 can vibrate and/or move the transducer horn 163, as further described herein. However, in other embodiments, the transducer assembly 150 can utilize a variety of other methods to produce an ultrasonic vibration such as, for example, magnetostrictive, pneumatic, hydraulic, and/or the like, as are known to those skilled in the art.

The bolt 158 further defines a lumen 159 such that a proximal end portion of the bolt 158 can receive a distal end portion of the flow tube 157. In this manner, the lumen 159 defined by the bolt 158 and the flow tube 157 collectively place the lumen 166 defined by the transducer horn 163 in fluid communication with the connector 156. Thus, the lumen 166 of the transducer horn 163 can be placed in fluid communication with a volume substantially outside of the proximal end of the housing 151.

As shown in FIGS. 1 and 2, the probe assembly 110 includes at least a transmission member 120 and a coupler 130. The coupler 130 includes a proximal end portion 131 and a distal end portion 132 and defines a lumen 133 that extends therethrough. The proximal end portion 131 of the coupler 130 is disposed within the lumen 166 at the distal end portion 165 of the transducer horn 163 and forms a threaded fit with the inner surface of the transducer horn 163 that defines the lumen 166. The distal end portion 131 of the coupler 130 is configured to receive a portion of the transmission member 120 to fixedly couple the transmission member 120 to the coupler 130. In this manner, the probe assembly 110 can be removably coupled to the transducer assembly 150 via the coupler.

The transmission member 120 is an elongate tube having a proximal end portion 121 and a distal end portion 122. The transmission member 120 can be any suitable shape, size, or configuration. In some embodiments, the transmission member 120 can optionally include any suitable feature configured to increase the flexibility (e.g., decrease the stiffness) of at least a portion of the transmission member 120, thereby facilitating the passage of the transmission member 120 through a tortuous lumen within a patient (e.g., a urinary tract, a vein, artery, etc.). For example, any of the transmission members shown and described herein can include any of the feature shown and described in U.S. patent application Ser. No. 13/652,881, entitled "Apparatus and Methods for Transferring Ultrasonic Energy to a Bodily Tissue," filed on Oct. 16, 2012, which is incorporated by reference herein in its entirety. For example, in some embodiments, a first portion of the transmission member 120 can be formed from a material having a lower stiffness than a material from which a second, different portion of the transmission member 120 is formed. In some embodiments, the stiffness of a portion of the transmission member 120 can be reduced by defining an opening (e.g., notch, a groove, a channel, a cutout, or the like), thereby reducing the area moment of inertia of the portion of the transmission member 120.

Figure 3:
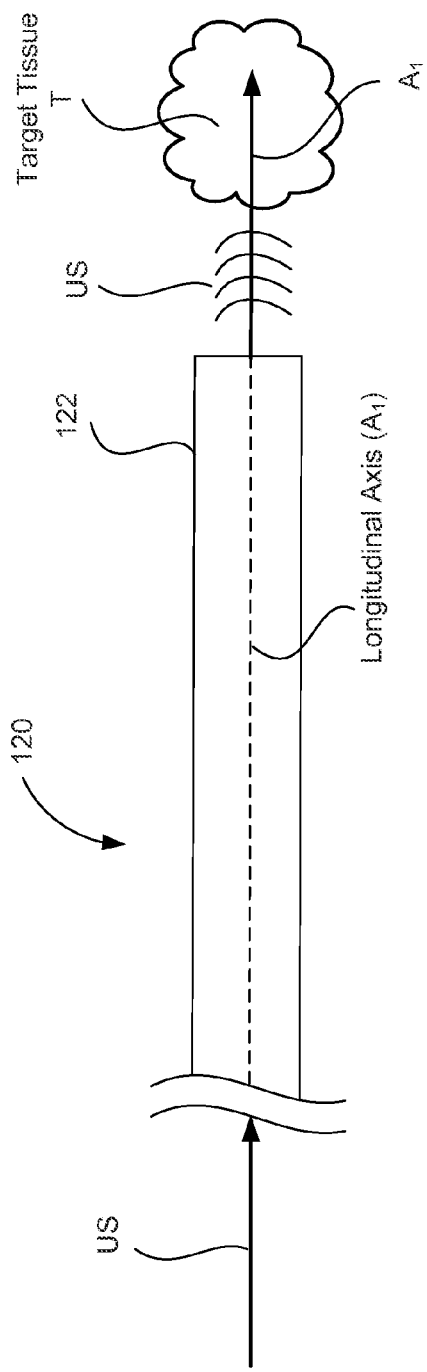
FIG. 3 is a schematic illustration of a portion of the transmission member shown in FIG. 1, which defines a longitudinal axis $A_1$.

FIG. 3 is a schematic illustration of a portion of the transmission member 120, which defines a longitudinal axis $A_1$. In use, a user (e.g., a surgeon, a technician, physician, etc.) can operate the ultrasonic system 100 (see FIG. 1) to deliver ultrasonic energy US to a target tissue T within a patient. The user can, for example, engage the pedals 172 of the foot switch 170 (see FIG. 1) such that the ultrasonic generator 180 generates and/or conveys an alternating current (AC) and/or voltage having the desired characteristics (e.g., a frequency up to approximately 20,000 Hz to 35,000 Hz with a voltage of approximately 500-1500 VAC (RMS)) to the transducer assembly 150. As described above, the transducer assembly 150 produces and amplifies the ultrasonic energy US, which is conveyed to the probe assembly 110, and travels along the length of the transmission member 120.

As shown in FIG. 3, the distal end portion 122 of the transmission member 120 can be disposed within a portion of the patient adjacent to a target tissue T such that the transmission member 120 transfers at least a portion of the ultrasonic energy US to the target tissue T. For example, in some embodiments, a distal tip of the transmission member 120 can impact a target tissue T, for example, to break apart an occlusion associated with the target tissue T. In some embodiments, the movement of the distal end portion 122 of the transmission member 120 produces cavitations within the portion of the patient. In this manner, the cavitations can further break apart and/or ablate the target tissue T. Cavitations are voids or bubbles produced by the inability of the fluid around the distal portion of the transmission member 122 to overcome the stresses induced by the motion of the transmission member 120. The collapse of the cavitation bubbles in and around cellular or other biological material that comprises the target tissue T produces a shockwave that erodes or fragments the target tissue T. In some embodiments, the ultrasonic system 100 can optionally be used to aspirate and/or to supply irrigation to a target tissue site, thus allowing the fragmented target tissue T to be removed from the body.

Figure 4:
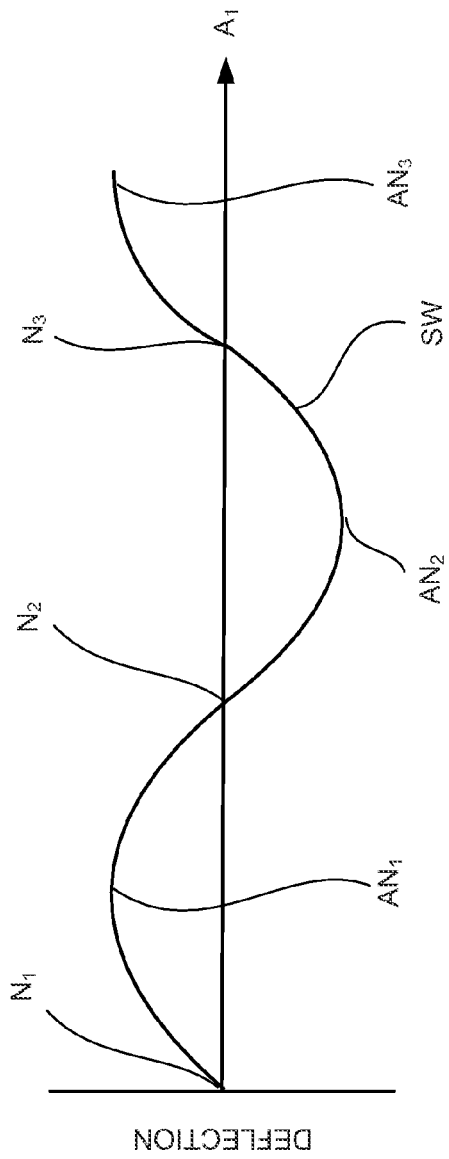
FIG. 4 is a graph depicting the deflection of the transmission member shown in FIGS. 1 and 3 about the longitudinal axis $A_1$.

When the ultrasonic system 100 is in use, an ultrasonic energy signal or wave US travels along the length of the transmission member 120. In some embodiments, the frequency of the ultrasonic wave (or signal) US is selected and/or controlled to substantially match the natural frequency of the ultrasonic energy delivery assembly 105, the ultrasonic transducer assembly 150, and/or the probe assembly 110 such that a resonance condition is produced within at least a portion of the transmission member 120. Thus, in use, the conveyance of the ultrasonic energy US to the transmission member 120 can be considered as producing a standing wave formed along the length of the transmission member 120. FIG. 4 is a graph showing a representation of the standing wave SW by depicting the deflection of the transmission member 120 about the longitudinal axis $A_1$.

As shown in FIG. 4, the standing wave SW produces a series of vibrational nodes (identified as nodes $N_1$, $N_2$, and $N_3$ in FIG. 4) and vibrational anti-nodes (identified as anti-nodes $AN_1$, $AN_2$, and $AN_3$ in FIG. 4) along the longitudinal axis $A_1$ of the transmission member 120. The location of the nodes along the transmission member 120 correspond to locations and/or regions of minimal displacement (or limited vibration) of the transmission member 120 when in use. The location of the anti-nodes along the transmission member 120 correspond to locations and/or regions where there is maximum displacement (or maximum vibration) of the transmission member 120 when in use. Thus, the anti-nodes, one of which can be located at the distal portion 122 (or the tip) of the transmission member 120, can produce cavitations in the biological fluids in contact with the transmission member 120 (e.g., blood, interstitial fluid, etc.), and the cavitations of the fluids can cause the destruction of adjacent biological target tissue (e.g., target tissue T in FIG. 3). The graph of FIG. 4 is presented for illustration only, and thus the standing wave SW is presented as having an amplitude along an axis substantially normal (i.e., lateral to) the longitudinal axis $A_1$, In use, the direction of vibration can be along the longitudinal axis $A_1$, a lateral axis or any other suitable direction.

As shown in FIG. 4, certain portions of the transmission member are subject to relatively large vibrations and/or displacement due to the location of the anti-nodes. Accordingly, these portions of the transmission member 120 are therefore subject to high stress. As a result, the regions of the transmission member 120 at which the anti-nodes are located can be potentially subject to reduced reliability, fracture and/or breakage. Hence, in some embodiments, an ultrasonic energy transmission system can be configured to spatially vary the location of the nodes and/or anti-nodes during operation of the system. For example, in some embodiments, the ultrasonic generator 180 is configured to vary the frequency (i.e., the driving frequency) of the electronic signal ES sent to the transducer assembly 150 within a range about the natural frequency of the ultrasonic energy delivery assembly 105, the transducer assembly 150 and/or the probe assembly 110 such that position of a vibrational node and/or a vibrational anti-node along the longitudinal axis $A_1$ of the transmission member 120 varies during the operation of the ultrasonic system 100. In other embodiments, an ultrasonic energy transmission system 100 can be configured to vary the characteristics of the transmission member 120 during use to spatially vary the position of a node or anti-node. For example, in some embodiments, the system 100 can include a damper or other component configured to vary the location of the nodes and/or anti-nodes during operation of the system. The variation of the nodes and/or anti-nodes is described in greater detail in FIG. 5.

Figure 5:
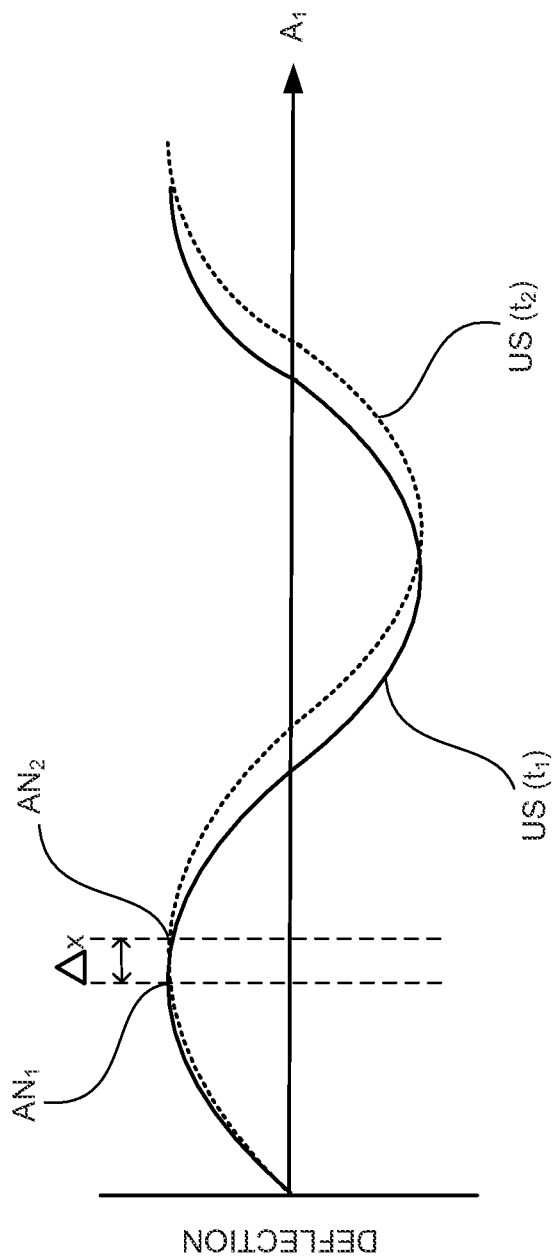
FIG. 5 is plot of the change in position of the anti-nodes along the longitudinal axis $A_1$ of a portion of the transmission member shown in FIGS. 1 and 3 when operated according to an embodiment.

FIG. 5 is plot representing the change in position of the anti-nodes along the longitudinal axis $A_1$ of a portion of the transmission member 120 during use according to any of the methods and apparatus described herein. More particularly, FIG. 5 shows a plot of an ultrasonic energy transmission wave along the longitudinal axis $A_1$ of the transmission member 120 at a first time, which is shown as the solid waveform identified as $US(t_1)$. FIG. 5 also shows the ultrasonic energy transmission wave at a second time as the dotted waveform identified as $US(t_2)$. Although the waveform US is presented as having an amplitude along an axis substantially normal (i.e., lateral to) the longitudinal axis $A_1$, it is understood that the direction of ultrasonic energy can be along the longitudinal axis $A_1$, a lateral axis or any other suitable direction along the transmission member 120. As shown in FIG. 5, the change in characteristics of the ultrasonic signal US results in a change in the spatial location of the anti-nodes in the standing waves created along the length of the transmission member 120. In particular, this is shown by the shift identified as $\Delta x$ between the anti-node $AN_1$ (which occurs at the first time) and the anti-node $AN_2$ (which occurs at the second time). This results in more uniform spatial distribution of the locations and/or regions of high stress along the longitudinal axis $A_1$ of the transmission member 120 than when the system is operated at a constant frequency setting. As a result, certain locations of the transmission member 120 do not repeatedly experience maximum vibrations and the high stress associated with an anti-node. Thus, when operated according to the methods described herein, the transmission member 120 can experience improved reliability.

In addition, dynamically varying the location of the nodes and/or anti-nodes according to the embodiments described herein can improve the effectiveness of the system in ablating tissue. In particular, by changing the location of the anti-nodes, the displacement and/or vibration profile of the transmission member 120 can be increased, thereby improving the function of the system. The increase in displacement can be caused, for example, by an overshoot in the amplitude of the standing wave resulting from the continuing shifting of the standing wave in the time domain.

The time interval between the variation in the nodes and/or anti-nodes (i.e., the difference between the first time and the second time) can be any suitable value. For example, in some embodiments, the time interval between the ultrasonic signal $US(t_1)$ and the ultrasonic signal $US(t_2)$ can vary between approximately 10 milliseconds and 300 milliseconds. Moreover, although shown as varying the location of the anti-nodes only once (i.e., between the first time and the second time), in other embodiments, the location of the anti-nodes can be varied continuously (at each time interval) during the operation of the system.

As described above, the ultrasound signal $US(t_1)$, $US(t_2)$ can be generated by the transducer assembly 150 as a result of an electronic signal ES sent from the ultrasonic generator 180 to the transducer assembly at a first time $t_1$ and at a second time $t_2$. In some embodiments, the change and/or offset in the location of the anti-nodes can be produced by changing the driving frequency of the electronic signal ES from an initial frequency at time $t_1$ to a second frequency at time $t_2$. Moreover, as discussed above, the driving frequency of the electronic signal ES can be varied continuously during the operation of the device, at any suitable time increment. In particular, in some embodiments, the variation in the frequency of the electronic signal ES and/or the ultrasonic signal US can be based on a random number, thereby ensuring that the locations of maximum stress are varied randomly. In other embodiments, the variation in the frequency of the electronic signal ES and/or the ultrasonic signal US can be based on a predetermined pattern of variation.

Figure 6:
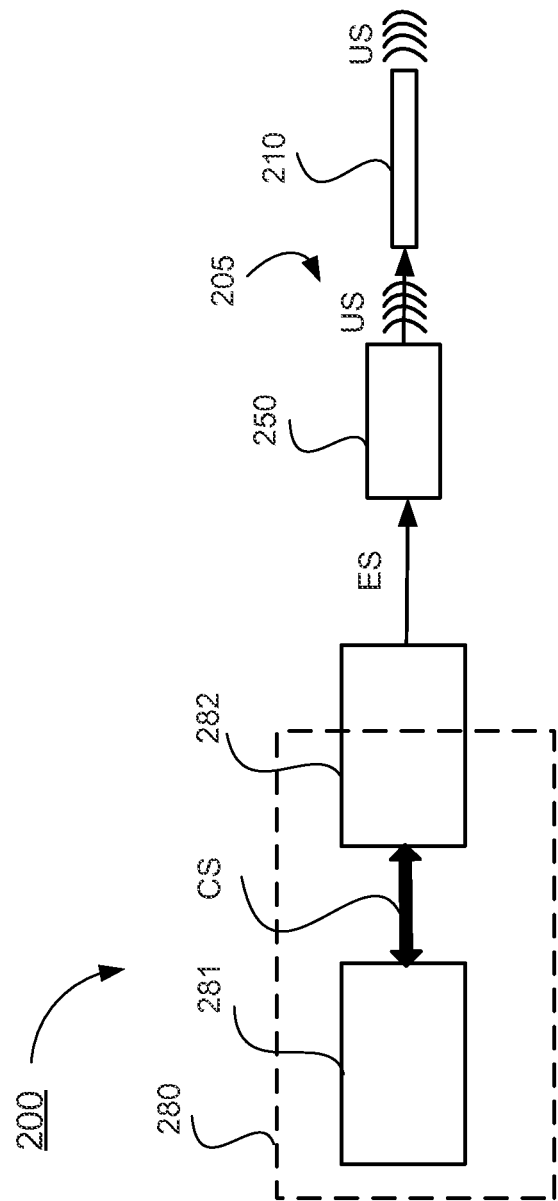
FIG. 6 is a schematic illustration of a system for delivering ultrasonic energy to a bodily tissue according to an embodiment.

In some embodiments, an ultrasonic energy ablation system includes an ultrasonic generator configured to produce a control signal to randomly vary the driving frequency of the electronic signal conveyed to an ultrasonic transducer assembly. In this manner, the system can spatially vary the location of the vibration nodes and/or anti-nodes in response to the control signal. For example, FIG. 6 is a schematic illustration of an ultrasonic ablation system 200, according to an embodiment. The ultrasonic energy ablation system 200 (also referred to herein as "ultrasonic system" or simply "system") includes an ultrasonic generator 280, and an ultrasonic energy delivery assembly 205.

The ultrasonic energy delivery assembly 205 includes an ultrasonic transducer assembly 250 and a probe assembly 210. The probe assembly 210 includes at least a transmission member or any suitable probe of the types shown herein. The transmission member can have increased flexibility to facilitate the passage of the probe assembly 210 through a tortuous lumen within a patient as shown and described in U.S. patent application Ser. No. 13/652,881, entitled "Apparatus and Methods for Transferring Ultrasonic Energy to a Bodily Tissue," filed on Oct. 16, 2012, which is incorporated by reference herein in its entirety. For example, in some embodiments, the probe assembly 210 can include a monolithically-constructed transmission member defining a lumen along a longitudinal axis that can provide aspiration from and/or irrigation to a target tissue site during an ultrasonic procedure. In other embodiments, the stiffness of a portion of the transmission member can be reduced by defining an opening (e.g., a notch, a groove, a channel, a cutout, and/or the like), thereby reducing the area moment of inertia of the portion of the transmission member. The probe assembly 210 can include any suitable coupler (not shown in FIG. 6) to operably couple the transmission member to the ultrasonic transducer assembly 250.

The ultrasonic transducer assembly 250 is operably coupled to the ultrasonic generator 280, such as, for example, via a cable, a wireless connection or the like. In this manner, the transducer assembly 250 can receive the electrical signal ES (i.e., the driving voltage and/or current) from the ultrasonic generator 280. The transducer assembly 250 is configured to produce and amplify an ultrasonic energy signal US in response to receiving the electric signal ES, and transfer the ultrasonic energy signal US to the probe assembly 210. The ultrasonic transducer assembly 150 can be any suitable assembly of the types shown and described herein.

The ultrasonic generator 280 includes a control module 281 that is operably coupled to a power module 282. The power module 282 can be any suitable hardware module and/or software module (stored in memory and/or executed in a processor of the ultrasonic generator 280) configured to produce the electronic signal ES to be received by the ultrasonic energy delivery assembly 205. Similarly stated, the power module 282 is configured to produce the driving electronic signal ES that is received by the ultrasonic energy delivery assembly 205. More particularly, the power module 282 and/or the power module 282 in conjunction with the generator 280 can produce the electronic signal ES having the desired characteristics (e.g., frequency, amplitude or the like) such that, when received by the transducer assembly 250, the desired ultrasonic energy signal US is produced. As described below, the power module 282 can produce and/or send the electronic signal ES having a frequency such that the ultrasonic energy signal US is at or near the natural frequency of the ultrasonic energy delivery assembly 205 and/or any of the components contained therein.

The control module 281 is configured to send a control signal CS to the power module 282 to randomly vary the frequency of the electronic signal ES within a range defined at least in part by the natural frequency of the ultrasonic energy delivery assembly 205 and/or any of the components therein. In this manner, the frequency of the ultrasonic energy signal US is randomly varied, which results in a shift in the spatial location of the vibration anti-nodes, as discussed above. Moreover, the dynamic and random variation of the ultrasonic energy signal US can improve the ablation performance of the system 200. The control module 281 can be a hardware module, such as an off-the shelf processor, an application specific integrated circuit (ASIC), a firmware, and/or a software module (stored in memory and/or executed in a processor of the ultrasonic generator 280) that performs the functions described herein.

The frequency of the electronic signal ES can be randomly varied about the natural frequency of the ultrasonic energy delivery assembly 205 and/or any of the components therein, in response to the control signal CS, by any suitable amount. Similarly stated, the control module 281 can be configured to produce and/or send the control signal CS such that the electronic signal ES is randomly varied about the natural frequency of the ultrasonic energy delivery assembly 205 within any suitable range. In some embodiments, the control module 281 is configured to vary the range within which the frequency of the electronic signal is varied.

Figure 7:
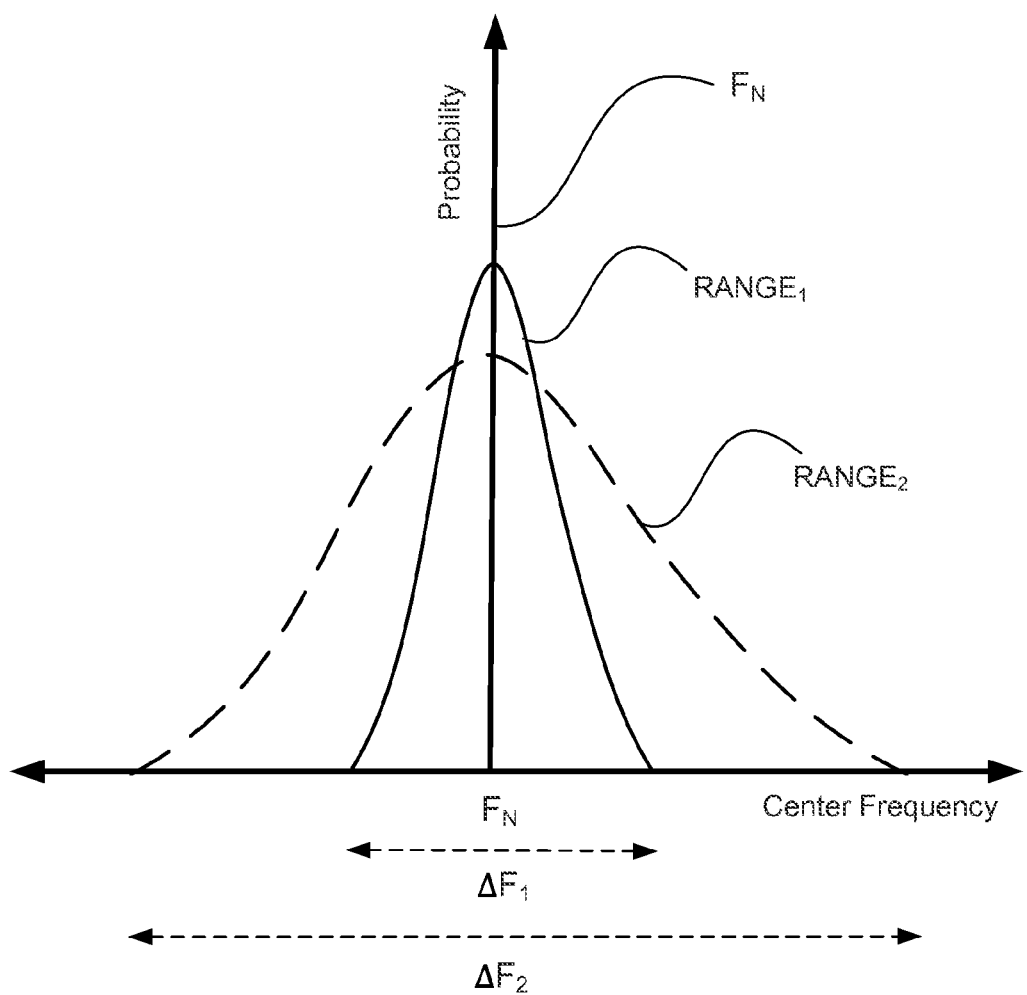
FIG. 7 is plot showing a variation in frequency of the ultrasonic energy conveyed through the transmission member shown in FIG. 6, when operated according to an embodiment.

For example, FIG. 7 is a graph showing two ranges of frequencies (identified as $RANGE_1$ and $RANGE_2$) within which the frequency of electronic signal ES can be randomly varied, according to an embodiment. Although the actual electronic signal ES is likely characterized by a number of different frequencies (i.e., when viewed in the frequency domain), the plot shown in FIG. 7 represents the probability of occurrence of the center (or nominal) frequency resulting from the random variation in response to the control signal CS. Similarly stated, the range of frequencies identified in FIG. 7 can also be considered as a frequency set point that is varied randomly in response to the control signal. In particular, FIG. 7 shows a plot of the nominal (or center) driving frequency of the electronic signal ES on the x-axis and the probability (or number of occurrences) on the y-axis. The variation in the center (or nominal) frequency of the electronic signal ES is centered about the natural frequency $F_N$ of the ultrasonic energy delivery assembly 205. The plot shows a first distribution or range (identified as $RANGE_1$), which corresponds to a frequency range of $\Delta F_1$, and a second distribution or range (identified as $RANGE_2$), which corresponds to a frequency range of $\Delta F_2$.

The first range $RANGE_1$ depicts a normal distribution of the center (or nominal) frequency of the electronic signal ES over a range $\Delta F_1$. The range $\Delta F_1$ can be any suitable range, such as for example, approximately ±two percent of the natural frequency $F_N$, approximately ±ten percent of the natural frequency $F_N$, approximately ±15 percent of the natural frequency $F_N$ or any suitable range from two to 15 percent of the natural frequency $F_N$. The second range $RANGE_2$ also depicts a normal distribution of the center (or nominal) frequency of the electronic signal ES over a range $\Delta F_2$. As shown in FIG. 7, the range $\Delta F_2$ is greater than the range $\Delta F_1$. Thus, in use, the magnitude of the spatial variation of the location of the nodes and/or anti-nodes along the probe assembly 210 resulting from the variation of the electronic signal ES within the second range $\Delta F_2$ can be greater than the magnitude of the spatial variation of the location of the nodes and/or anti-nodes resulting from the variation of the electronic signal ES within the first range $\Delta F_1$. The second range $\Delta F_2$ can be any suitable range, such as for example, approximately ±two percent of the natural frequency $F_N$, approximately ±ten percent of the natural frequency $F_N$, approximately ±15 percent of the natural frequency $F_N$, approximately ±25 percent of the natural frequency $F_N$ or any suitable range from two to 25 percent of the natural frequency $F_N$.

Although only two ranges of frequency deviation are shown in FIG. 7, in other embodiments, the control signal can result in any number of different ranges within which the center (or nominal) frequency of the electronic signal ES and/or a control set point associated with the control signal CS can be varied. Moreover, although shown as being a substantially normal distribution about the natural frequency $F_N$, in other embodiments, the center (or nominal) frequency of the electronic signal ES can be randomly varied according to any suitable distribution.

As described above, in some embodiments, the control signal is associated with a frequency set point. Thus, in such embodiments, the normal distribution of frequency (e.g., $\Delta F_1$ and $\Delta F_2$) about the natural frequency $F_N$ of the ultrasonic energy delivery assembly 205 as shown in FIG. 7 may not be the deviation of the center frequency of the electronic signal ES, but rather can be the random variation (or deviation) of a frequency set point associated with the control signal CS. The actual deviation of the electronic signal ES and/or the resulting ultrasonic energy signal US that is transmitted via the probe assembly 210 can differ from the frequency set point as a result of delay and/or inertia associated with the electrical and/or mechanical systems.

In some embodiments, the control module 281 can be configured to send a control signal CS that varies as a function of time. In such embodiments, the control signal CS can be, for example, a continuous signal with varying frequency and/or amplitude at regular (periodic) time intervals or irregular (aperiodic) time intervals. In other embodiments, the control module 281 can be configured to send control signals CS that are a series of discrete electronic signals that are generated by the control module 281 at discrete time intervals such as, for example, at an interval of between approximately every 10 milliseconds and approximately every 300 milliseconds. In such embodiments, each of the successive discrete control signals (CS) can result in a different, randomly varying, set point that is received by the power module 282 and used to randomly vary the frequency of the electronic signal ES (and ultimately the ultrasonic energy signal US), as described herein.

The ultrasonic generator 280 can be any of the generators described herein, and can be operated according to any of the methods described herein. In some embodiments, the ultrasonic generator 280 can include the power module 282. The ultrasonic generator 280 can include a processor, a memory and the circuitry (not shown in FIG. 6) to produce the electronic signal ES (i.e., a current and/or a voltage) having the desired characteristics that can be received by the ultrasonic transducer assembly 250 and converted into ultrasonic energy (US). As described in detail herein, the ultrasonic generator 280 (or "generator") is configured to generate, control, amplify, and/or transfer the electronic signal ES (e.g., a voltage or current) to the transducer assembly 250 as shown in FIG. 6.

Although not explicitly shown in FIG. 6, in some embodiments, the ultrasonic generator 280 and/or the power module 281 can include the electronic circuitry, hardware, firmware and/or instructions to cause the ultrasonic generator 280 to act as a frequency inverter and/or voltage booster. In this manner, the ultrasonic generator 280 and/or the power module 281 can produce and/or output a voltage to the transducer assembly 250 having the desired characteristics to produce the desired ultrasonic energy output. For example, in some embodiments, the ultrasonic generator 280 can receive AC electrical power at a frequency of approximately 60 Hz and a voltage of approximately 120V and convert the input electrical power to a frequency up to approximately 20,000 Hz to 35,000 Hz with a voltage of approximately 500-1500 VAC (RMS). Thus, the ultrasonic generator 280 and/or the power module 281 can supply the transducer assembly 250 with an AC electrical power signal having an ultrasonic frequency.

As described below in greater detail, in some embodiments, the frequency of the electrical signal ES can be varied randomly by the control module 281 based at least in part on a random value generated and/or received by the control module 281. In some embodiments, the generator 280 and/or the control module 281 can include a random number generator (not shown in FIG. 6). The random number generator can be, for example, a software module stored in a memory and/or executed in a processor of the ultrasonic generator 280 that is operably coupled to the control module 281. Such a software random number generator module can implement a multitude of computational methods to generate a sequence of numbers that approximate the properties of random numbers. Such computational methods can include, for example, deterministic random bit generator (DRBG), linear congruential generators, lagged Fibonacci generators, linear feedback shift registers, and/or the like.

In other embodiments, for example, the random number generator can be a hardware module (i.e., a hardware random generator device) that generates random numbers from a physical process, rather than from a computational method. Such modules can be based on microscopic phenomena that can generate a low-level, statistically random "noise" signal, such as thermal noise or the photoelectric effect or other quantum phenomena. Such hardware random number generator modules (or devices) can typically include a transducer to convert some aspect of the physical phenomena to an electrical signal, an amplifier and other electronic circuitry to increase the amplitude of the random fluctuations to a macroscopic level, and some type of analog to digital converter to convert the output into a digital number. By repeatedly sampling the randomly varying signal, a series of random numbers can obtained.

In some embodiments, the ultrasonic generator 280 can include a noise detection module operatively coupled to the control module (not shown in FIG. 6). Such noise detection modules, which are described in more detail below, can be implemented at least in part in the hardware, and can include at least one of a sensor, an amplifier, a filter or an analog to digital converter. The noise detection module can be configured to produce a noise signal associated with a noise component of the electronic signal ES produced by the power module. In use, the control signal CS is based at least in part on the noise signal, thereby resulting in random variation of the electronic signal ES. In particular, in such embodiments, the randomness of the noise component of the electronic signal ES can be used by the control module 281 to slightly vary the frequency of the electronic signal ES sent from the power module 282 to the ultrasonic transducer assembly 250. Accordingly, in use, the position of the vibrational nodes and/or vibrational anti-nodes along the longitudinal axis $A_1$ of the transmission probe 210 can be varied.

Figure 8:
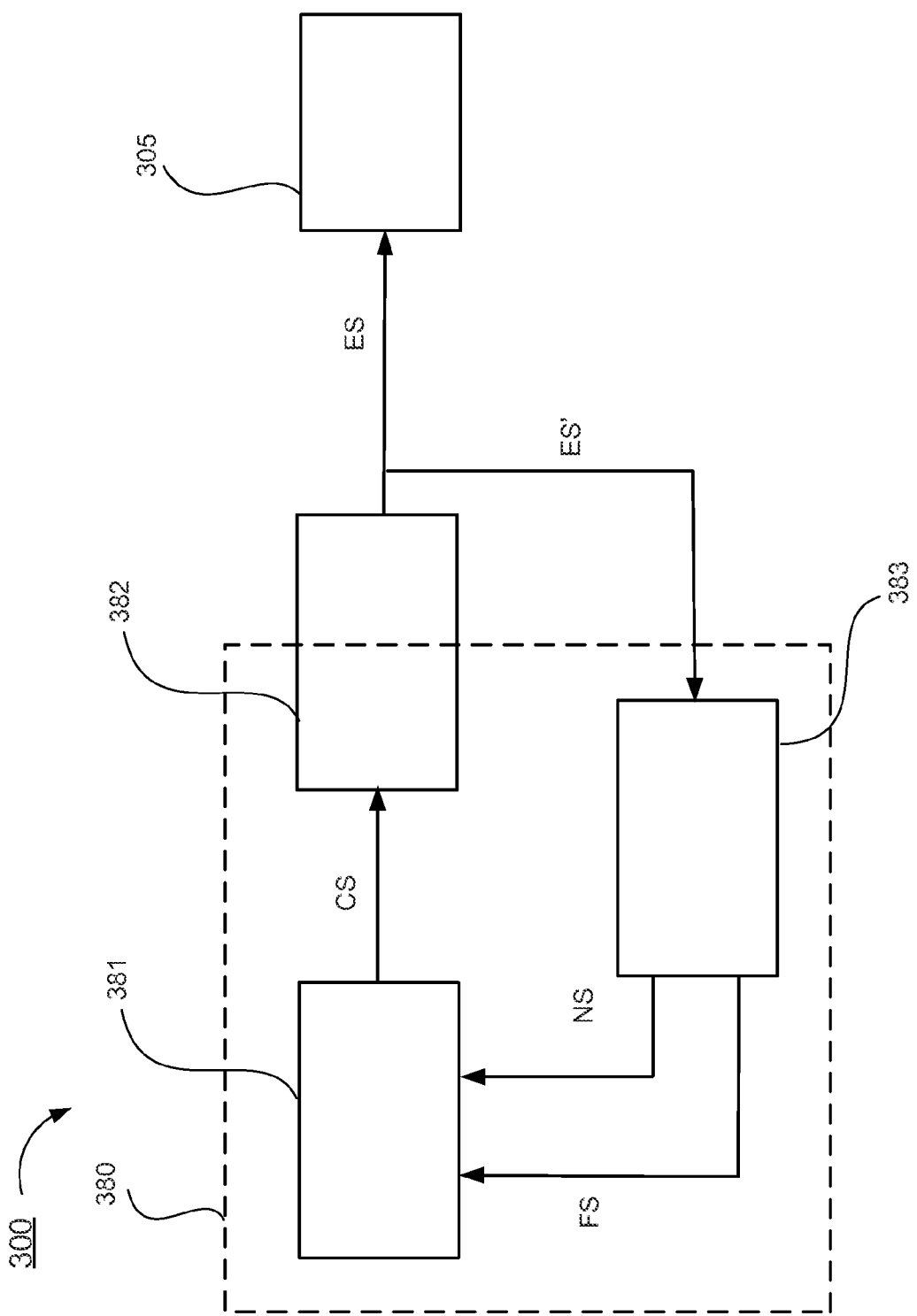
FIG. 8 is a schematic illustration of a generator of an ultrasonic energy delivery system according to an embodiment.

In some embodiments, an ultrasonic generator can include a feedback module configured to send a feedback signal to a control module therein. The feedback module can, for example, provide feedback that is used to determine the natural frequency of an ultrasonic energy delivery assembly and/or to vary the frequency of an electronic signal sent to an ultrasonic transducer. For example, FIG. 8 is a schematic illustration of an ultrasonic ablation system 300, according to an embodiment. The ultrasonic energy ablation system 300 (also referred to herein as "ultrasonic system" or simply "system") includes an ultrasonic generator 380 that is operably coupled to a power module 382. The power module 382 is configured to produce an electronic signal ES that is received by an ultrasonic energy delivery assembly 305. The ultrasonic energy delivery assembly 305 can be any of the ultrasonic energy delivery systems shown and described herein. For example, the ultrasonic energy delivery assembly 305 can include an ultrasonic transducer assembly (e.g., similar to the transducer assembly 150), a probe assembly (similar to the probe assembly 210), a transmission member (similar to the transmission member 220) or the like. The ultrasonic energy delivery assembly 305 (and/or any of the components therein) is characterized by a natural frequency.

The ultrasonic generator 380 includes a control module 381 and a feedback module 383 that is operatively coupled to the control module 381. The ultrasonic generator 380 is operably coupled to a power module 382 that is configured to produce an electronic signal ES that is received by an ultrasonic energy delivery assembly 305. The power module 382 can be any suitable hardware module and/or software module (stored in memory and/or executed in a processor of the ultrasonic generator 380) configured to produce the electronic signal ES to be received by the ultrasonic energy delivery assembly 305. Similarly stated, the power module 382 is configured to produce the driving electronic signal ES that is received by the ultrasonic energy delivery assembly 305. More particularly, the power module 382 and/or the power module 382 in conjunction with the generator 380 can produce the electronic signal ES having the desired characteristics (e.g., frequency, amplitude or the like) such that, when received by the transducer assembly 350, the desired ultrasonic energy signal is produced.

The feedback module 383 is configured to measure and/or detect at least a portion of the electronic signal ES (the portion being measured, detected and/or analyzed is identified as the signal ES') and produce a feedback signal FS and a noise signal NS. The feedback signal FS is associated with a nominal component of the electronic signal ES produced by the power module 382. For example, the feedback signal FS can be associated with (and/or a measure of) the nominal current or voltage of the electronic signal ES. The noise signal NS is based, at least in part, on a noise component of the electronic signal ES produced by the power module 382. As discussed in more detail below, the feedback module 383 can include any suitable software, firmware and/or hardware to produce the feedback signal FS and the noise signal NS. For example, in some embodiments, the feedback module 383 is implemented at least in part in hardware, and includes a sensor, an amplifier, a filter and/or an analog to digital converter.

The control module 381 is configured to send a control signal CS to the power module 382 to randomly vary the frequency of the electronic signal ES within a range defined at least in part by the natural frequency of the ultrasonic energy delivery assembly 305 and/or any of the components therein. In this manner, the frequency of the ultrasonic energy signal US is randomly varied, which results in a shift in the spatial location of the vibrational anti-nodes, as discussed above. In particular, the control module 381 is configured to determine the natural frequency (e.g., natural frequency $F_N$ as depicted in FIG. 7) of the ultrasonic energy delivery assembly 305 based on the feedback signal FS. The control module 381 can determine the natural frequency of the ultrasonic energy delivery assembly 305 in any suitable manner. In some embodiments, for example, the control module 381 can produce a control signal, such as the control signal CS, in a manner that varies the frequency of the electronic signal ES according to a pattern, such as, for example, a sweep over a predetermined frequency range. The control module 381 receives the feedback signal FS, which can be associated with a current value of the electronic signal ES, at each frequency. In some embodiments, the control module 381 can determine the natural frequency as the frequency that corresponds to a peak current value of the electronic signal ES. The control module 381 can employ any other suitable method and/or algorithm for determining the natural frequency of the ultrasonic energy delivery assembly 305.

The control module 381 is also configured to send the control signal CS to the power module 382 to vary the frequency of the electronic signal ES within a range defined at least in part by the natural frequency of the ultrasonic energy delivery assembly 305. The control signal CS is based at least in part on the noise signal NS. In this manner, the frequency of the electronic signal ES can be varied such that the position of the vibrational nodes and/or vibrational anti-nodes within and/or along a portion of the ultrasonic energy delivery assembly 305 is randomly varied. By using the noise signal NS, which inherently contains a random nature, the control module 381 need not include a software-driven random number generator.

In particular, the random noise present in the electronic signal ES generated by the power module 382 can be random fluctuations in the electronic signal ES, which are detected via the signal ES', and which are then reflected in the noise signal NS. Such random noise can include, for example, thermal noise, shot noise, flicker noise, burst noise, avalanche noise, and/or the like. Thermal noise (Johnson-Nyquist noise) is generated by the random thermal motion of charge carriers (usually electrons), inside an electrical conductor, which happens in the presence of an applied voltage. Thermal noise is approximately white, and hence its power spectral density is nearly equal throughout the frequency spectrum. Shot noise in electronic devices is the result of unavoidable random statistical fluctuations of the electric current in an electrical conductor. Random fluctuations are inherent when current flows, as the current are a flow of discrete charges (electrons). Flicker noise is a signal or process with a frequency spectrum that falls off steadily into the higher frequencies. Flicker noise occurs in most electronic devices, and results from a variety of effects related to a direct current. Burst noise includes sudden step-like transitions between two or more levels (non-Gaussian), as high as several hundred microvolts, at random and unpredictable times. Each shift in offset voltage or current can last for several milliseconds, and the intervals between pulses tend to be in the audio range (less than 100 Hz). Avalanche noise is the noise produced when a junction diode is operated at the onset of avalanche breakdown, in which carriers in a high voltage gradient develop sufficient energy to dislodge additional carriers through physical impact, creating ragged current flows.

In use, the control module 381 can determine the natural frequency of the ultrasonic energy delivery assembly 305 at a first time ($t_1$) based on the feedback signal FS. In this manner, the control module 381 can account for variations in the natural frequency of the system resulting from natural variation in the components of the system, the environment or the like. The control module 381 can further generate a control signal CS, and send the control signal CS to the power module 382 at a second time ($t_2$), where the second time is after the first time ($t_1 < t_2$). In this manner, the control module can vary the frequency of the electronic signal ES within a range about the natural frequency of the ultrasonic energy delivery assembly 305.

In some embodiments, the generator 380, the feedback module 383 and/or the control module 381 can be configured to vary the range within which the frequency of the electronic signal ES is varied. For example, as discussed in more detail below, in some embodiments, a portion of the system 300 can include a filter module (e.g., located in the control module 381 or the feedback 383 module configured to limit the frequency range of the noise portion of electrical signal ES that is received via signal ES' and is included within the noise signal NS. Thus, in such cases, the characteristics of the filter function implemented by the filter module can impact the range of the noise signal NS upon which the control signal CS is at least partially based. For example, in some embodiments, a low pass-filter function can be implemented to reduce the amount of noise from the electronic signal ES that passes through the filter. Hence, the noise signal NS will have less random variation, and the variation of the electronic signal ES (resulting from the control signal CS) will be over a narrower range (such as, for example, $RANGE_1$ shown in FIG. 7) than would otherwise occur. In another example, a high pass filter function can be implemented to allow more noise to pass through the filter. Hence, noise signal NS will have greater random variation (than in a situation in which a low pass filter is employed), and the variation of the electronic signal ES (resulting from the control signal CS) will be over a greater range (such as, for example, $RANGE_2$ shown in FIG. 7) than would otherwise occur. In yet other cases, the range of frequencies of the electrical signal can be varied by any other suitable mechanism or algorithm.

In some embodiments, the control module 381 is configured to send the control signal CS to the power module 382 at control signal time intervals of between approximately 10 milliseconds and approximately 300 milliseconds. In some embodiments, the control module 381 can send control signals CS to the power module 382 such that the electronic signal ES generated by the power module 382 is a continuous signal with periodic changes in frequency based on the instructions contained in the control signal CS. In other embodiments, the control module 381 can send control signals CS to the power module 382 such that the electronic signal ES generated by the power module 382 is one of a series of discrete signals generated at periodic (or random) time intervals with a "dead" time occurring between successive electrical signals ES (or rather signal pulses). The control module 381 is also configured to vary the range within which the frequency of the electronic signal ES is varied by processing the noise signal NS and feedback signal FS received from the feedback module 383.

The ultrasonic generator 380 and any of the ultrasonic generators described herein include the electronic circuitry, hardware, firmware and or instructions to cause the ultrasonic generator to perform the functions described herein. (e.g., to act as a frequency inverter and/or voltage booster). In this manner, the ultrasonic generators described herein can produce and/or output a voltage to a transducer assembly having the desired characteristics to produce the desired ultrasonic energy output. For example, in some embodiments, the ultrasonic generator 380 (or any of the other generators described herein) can receive AC electrical power at a frequency of approximately 60 Hz and a voltage of approximately 120V and convert the voltage to a frequency up to approximately 20,000 Hz to 35,000 Hz with a voltage of approximately 500-1500 VAC (RMS).

Figure 9:
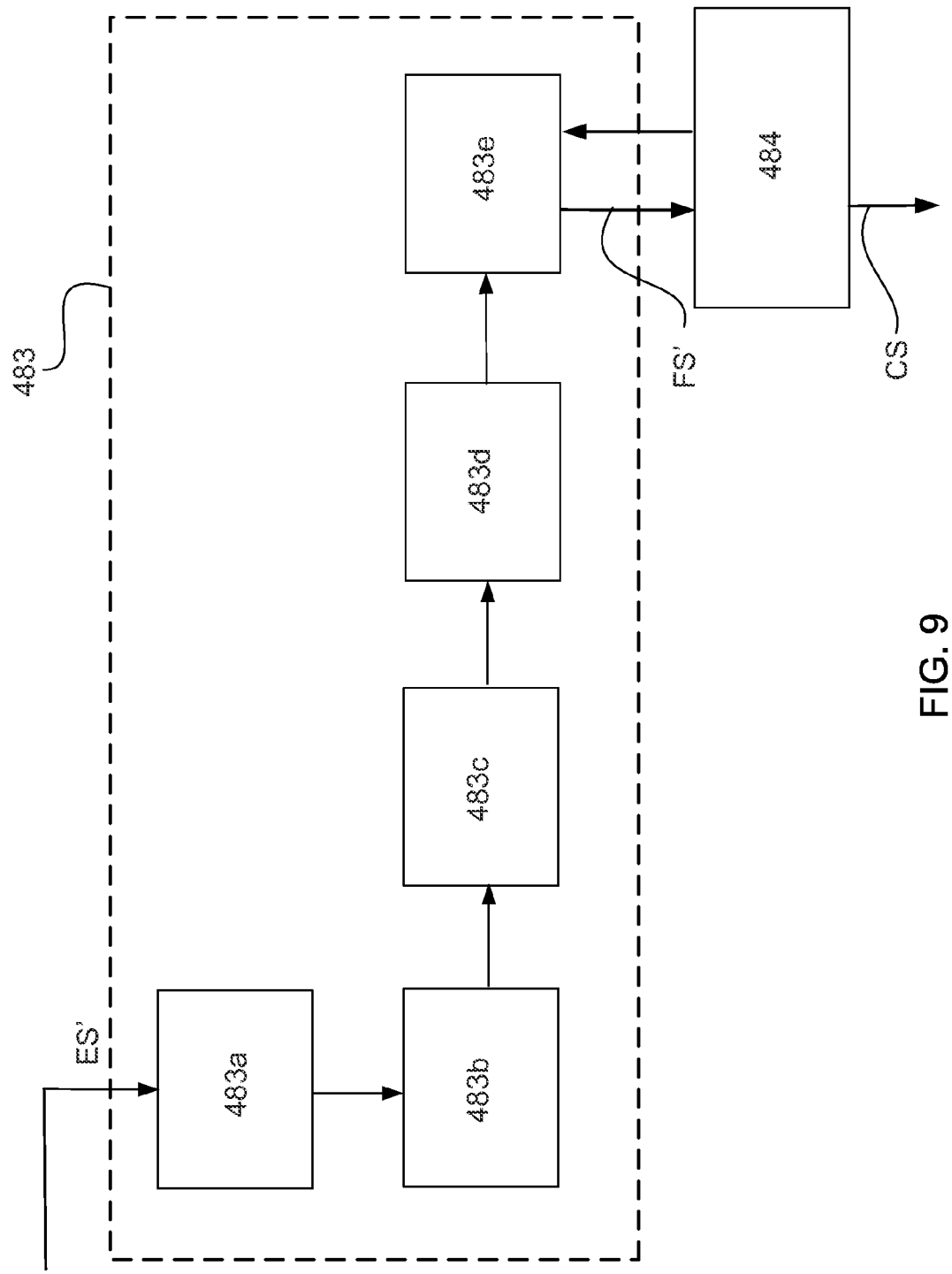
FIG. 9 is a block diagram of a feedback module that is implemented in hardware, according to an embodiment.

In some configurations, the feedback module 383 can be implemented as a software module that is stored in memory and/or executed in the processor of the ultrasonic generator 380 that cause the ultrasonic generator 380 to execute specific operations associated with varying the frequency of the electronic signal ES sent to the ultrasonic energy delivery assembly 305. In other configurations, the feedback module 383 can be implemented in part in hardware where the feedback module 383 can include at least one of a sensor, an amplifier, a filter and an analog to digital converter. For example, FIG. 9 is a block diagram of a feedback module 483 that is implemented in hardware, according to an embodiment. The feedback control module 483 includes sensor 483a, a voltage regulator 483b, a filter 483c, a voltage amplifier/divider 483d, and an analog to digital converter 483e. As shown in FIG. 9, the feedback module 483 is operably coupled to and transmits a feedback signal FS' to a microprocessor 484 of an ultrasonic generator (such as the generator 380 shown and described above). In some configurations, a control module within a generator (e.g., control module 381 in FIG. 9) can be implemented inside the microprocessor 484. The microprocessor 484 produces a control signal CS that is transmitted to a power module, as described above.

The sensor 483a detects a portion of the electrical signal sent by the power module to the ultrasonic energy delivery assembly (e.g., ES' in FIG. 8). The sensor 483a can be any kind of electronic sensor that can measure electrical current and/or voltage, such as, for example, a current sensor, a voltage detector, a galvanometer, and/or the like. In some embodiments, the voltage regulator 483b can be used to ensure the signal voltage level of the portion of the electronic signal ES' detected by the sensor 483a is above pre-set reference point.

The filter 483c can be any kind of filter such as a low-pass filter, a high-pass filter, a band-pass filter or a notch filter, and can be used to limit the range of frequencies detected in the electronic signal ES' that are conveyed to the processor 484 via a noise signal NS. As described above, the choice of the filter will influence the resulting system characteristics. In one example, a low pass-filter can be used to allow less noise to pass through the filter 483c. Hence, the noise component of the feedback signal FS' will have less random variation, and the variation of the electronic signal ES (produced in response to a control signal CS, as shown in FIG. 9) will be over a narrower range (such as, for example, $RANGE_1$ shown in FIG. 7) than would otherwise occur. In another instance, a high pass filter can be used to allow more noise to pass through the filter 483c. Hence, the noise component of the feedback signal FS' will have greater random variation (than in a situation in which a low pass filter is employed), and the variation of the electronic signal ES (resulting from the control signal CS) will be over a greater range (such as, for example, $RANGE_2$ shown in FIG. 7) than would otherwise occur.

The voltage amplifier/divider 483d can be included if the voltage level of the detected electrical signal ES' is too small or if the voltage level of the detected electronic signal ES' is higher than the input of the analog to digital (A/D) converter 483e allows. The analog to digital (A/D) converter 483e converts an analog input signal into a digital output signal by sampling the analog signal at higher than the Nyquist frequency.

The feedback signal FS' from the A/D converter 483e is the value of the actual electronic signal ES' in addition to random electronic noise. In some embodiments, the microprocessor can process the feedback signal FS' from the A/D converter 483e to produce a control signal CS as follows. First, the noise component of the feedback signal FS' is calculated according to the equation below:

$$Noise = I_R - I_N$$

where $I_R$ is the output signal from the A/D converter 483e (i.e., the feedback signal FS') and $I_N$ is the nominal value of the electronic signal. The change in the ultrasonic drive frequency $\Delta f$ as a result of receiving the feedback signal FS' is calculated as follows:

$$\Delta f = (Noise/Max) \times F$$

where Max is the maximum amplitude of the signal from the A/D converter 483 output, and F is the permissible frequency range (due to implementation of the filter 483c). The drive frequency $f_D$ for the next cycle of the electrical signal ES to be sent to the energy delivery assembly 305 can be calculated as follows:

$$f_D = f_r + \Delta f$$

where $f_r$ is the resonant frequency of the ultrasonic energy delivery assembly. As discussed above, in some embodiments, the resonant (or natural) frequency of the ultrasonic energy delivery assembly can be determined by the ultrasonic generator (and/or the microprocessor 484). In some configurations, a digital filter can be implemented in the microprocessor 484 in addition to or in lieu of the analog filters 483c implemented in the feedback module 483 and/or are not sufficient to filter the detected electronic signal ES'.

In some embodiments, the microprocessor 484 can control the functionality of the feedback module 483. Moreover, in some embodiments, the various components of the feedback module 483 inside the dotted line block in FIG. 10 can be implemented inside one integrated circuit (IC) chip. In some configurations, the A/D converter 483e can also be embedded in the microprocessor 484.

Figure 10:
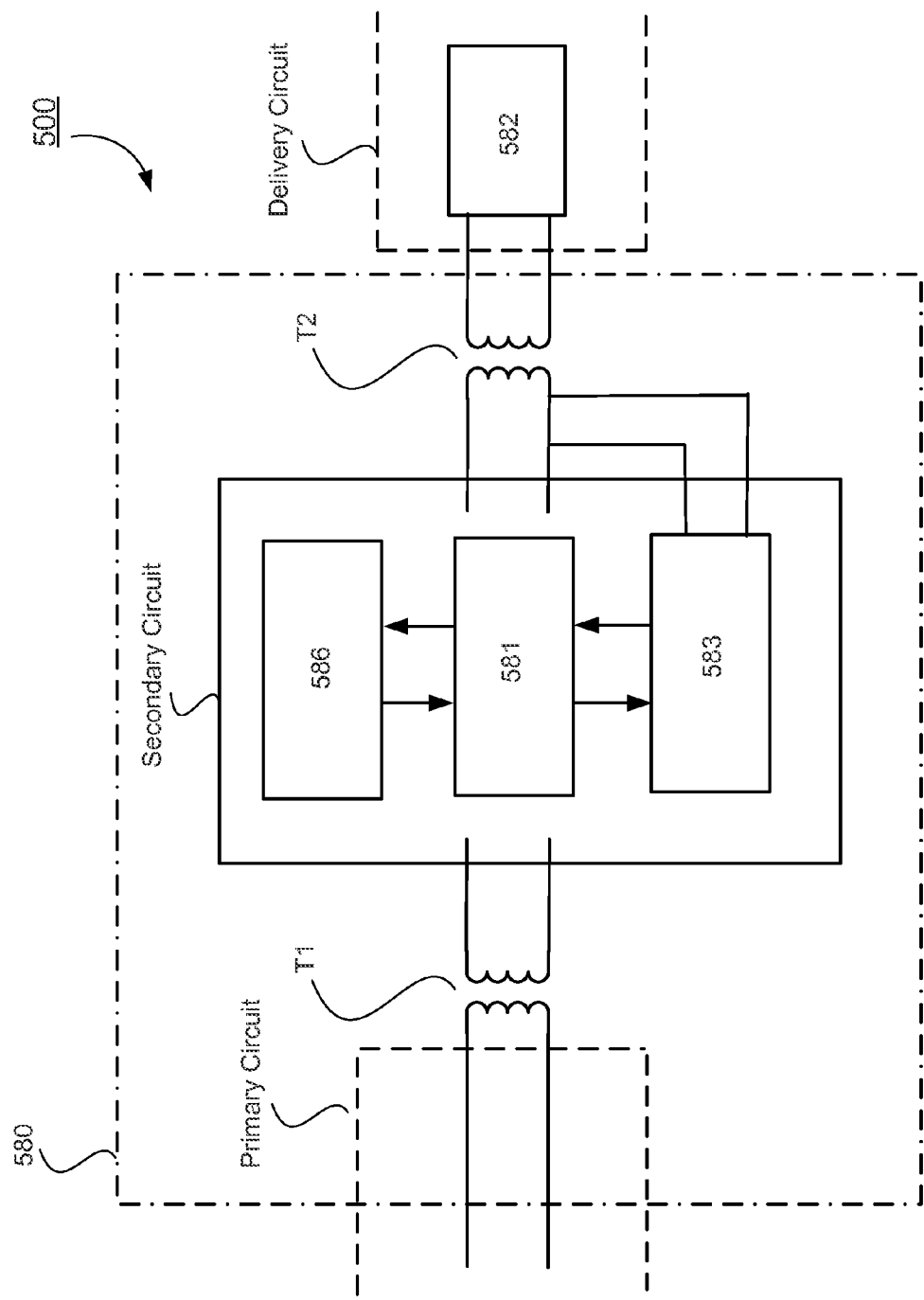
FIG. 10 is a block diagram of an ultrasonic energy delivery system 500, according to an embodiment.

Although the feedback modules 383, 483 are described as receiving feedback (including a noise component) based on the electronic signal ES sent by a power module, in other embodiments, any of the systems described herein can receive feedback from any suitable portion of the system. For example, FIG. 10 is a block diagram of an ultrasonic energy delivery system 500, according to an embodiment. The system 500 includes an ultrasonic generator 580 and a power module 582. The ultrasonic generator 580 includes a primary circuit, a secondary circuit and a delivery circuit (which also includes the power module 582). As described above, the ultrasonic generator 580 can function as a frequency inverter and voltage booster and can invert the input power signal frequency from 60 Hz and/or 50 Hz to over 20,000 Hz (i.e., an ultrasonic frequency). The primary circuit includes the power supply line from the electrical energy source such as, for example, power lines from an electrical generator or power lines from the wall power outlet. The power supply can include a standard direct (DC) power supply cord with an alternate current (AC) adapter that can be plugged into any standard wall power outlets. Transformer T1 can isolate the primary circuit from the secondary circuit, and in some instances can also be used to boost the magnitude of the input voltage received by the secondary circuit.

The delivery circuit includes the power module 582, which, as described above, receives a control signal from the ultrasonic generator 580 and/or any components therein. The power module 582 generates and sends an electronic signal to the ultrasonic energy delivery assembly (not shown in FIG. 10), which then generates the ultrasonic energy signal. The delivery circuit is connected to the secondary circuit within the generator 580 via transformer circuitry T2. The transformer circuitry T2 in the ultrasonic generator 580 can isolate the delivery circuit from the ultrasonic generator 580, and can also boost the voltage output from the ultrasonic generator 580.

The secondary circuit includes a control module 581, a feedback and/or noise detection module 583 and a user interface 586. The control module 581 is similar to the control module 381 described in FIG. 8 and control module 281 described in FIG. 6, and therefore is not be discussed in any further detail.

The user interface 484 can include, for example, a liquid crystal display (LCD) unit or a light emitting diode (LED) alpha-numeric display unit. In some embodiments, there can be only one display unit. In other embodiments, there can be multiple display units. The display unit can display a multitude of information to the user such as, for example, the natural frequency of the ultrasonic energy delivery assembly, the frequency of the electronic signal sent to the ultrasonic energy delivery assembly, ultrasound dosage levels such as ultrasound signal power level delivered at the treatment site, and/or the like.

Figure 11:
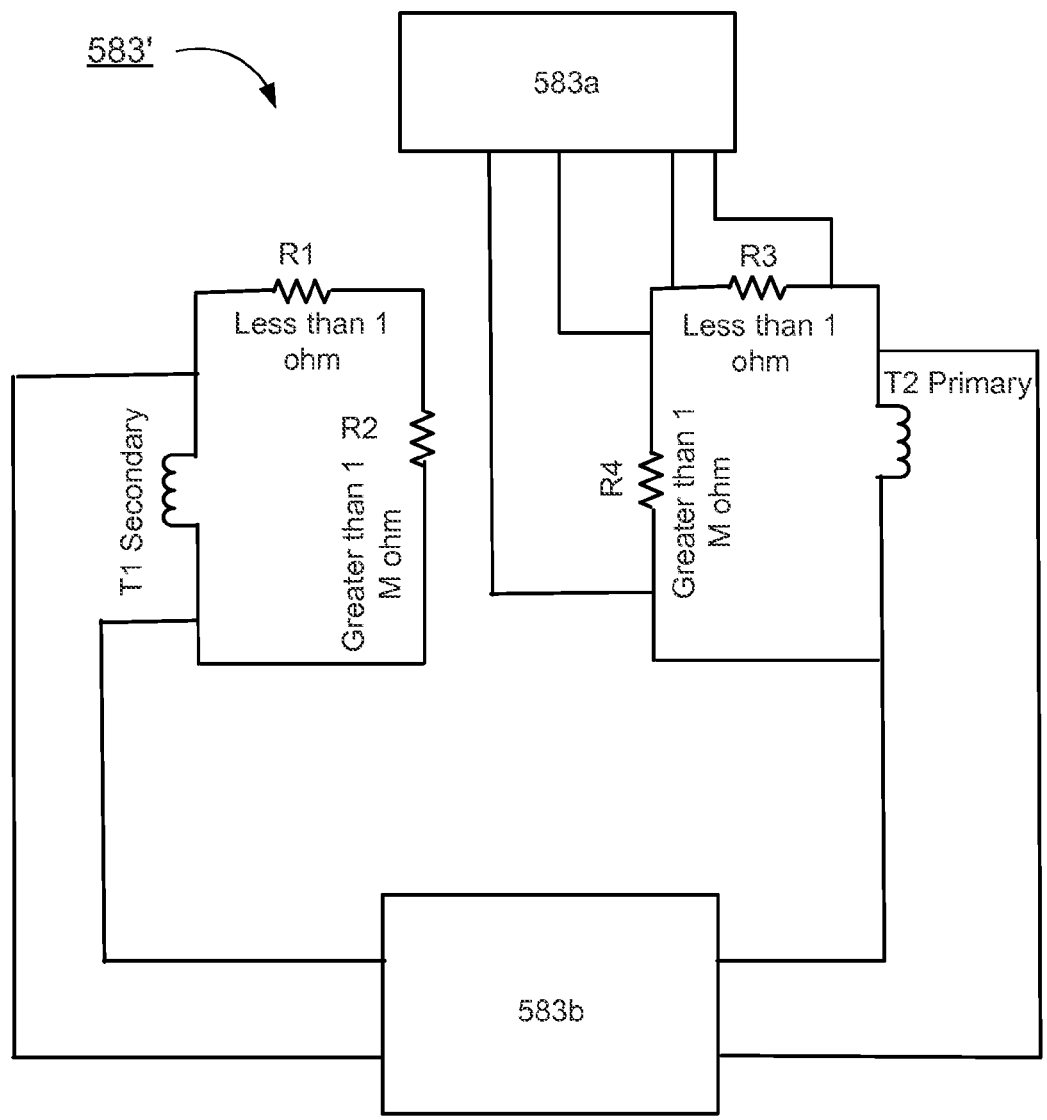
FIG. 11 is a block diagram of a feedback/noise detection module, according to an embodiment.

The feedback module 583 can be any suitable feedback module of the types shown and described herein, such as the feedback module 483 described with reference to FIG. 9. As shown in FIG. 10, the feedback module 583 is operably coupled to and/or within the secondary circuit, and receives input from the "primary" side of the transformer T2. Such an arrangement can enhance the safety and improve compliance with standards. Thus, the feedback module 583 receives as input the control signal and or any other signals produced by the control module. In other embodiments, however, the feedback signal can receive input from any portion of the system 500. For example, FIG. 11 is a block diagram of a feedback/noise detection module 583', according to an embodiment, which shows alternative locations for receiving input on which the control signal is based. As an example, the feedback/noise detection module 583' includes a first portion 583a that receives input from the "primary" side of the transformer T2.

Moreover, the feedback module 583 can include any circuitry and/or components for measuring a signal within and/or produced by any portion of the system. For example, as shown in FIG. 11, the feedback/noise detection module 583' can include a current sensor having a small value resistor (typically less than 1Ω as seen by resistors R1 and R3 in FIG. 11) in series connection with the transformer T1 and T2, respectively. In other configurations, the current sensor can also be a Hall Effect sensor. In some embodiments, the feedback/noise detection module 583' can include a voltage sensor that can have a large value resistor (typically greater than 1Ω as seen by resistors R2 and R4 in FIG. 12) in parallel connection with the transformer T1 and T2, respectively. As described herein, the feedback signals are used as sources for random noise which is used to vary the frequency of the electronic signal sent to an ultrasonic energy delivery assembly.

Figure 12:
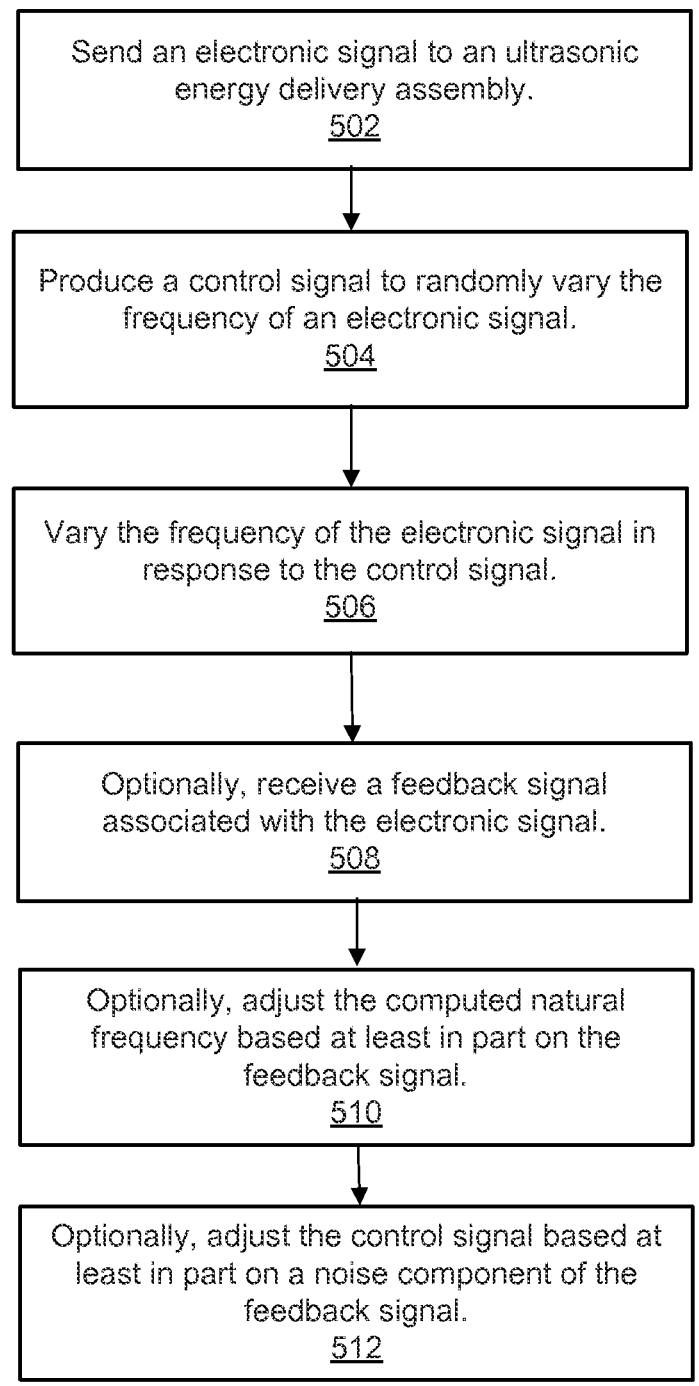
FIG. 12 is a flowchart illustrating a method of generating a control signal to vary the frequency of an electronic signal within an ultrasonic energy transmission system, according to an embodiment.

FIG. 12 is a flowchart illustrating a method of generating a control signal to vary the frequency of an electronic signal within an ultrasonic energy transmission system, according to an embodiment. The method 501 includes sending an electronic signal to an ultrasonic energy delivery assembly, at 502. The electronic signal can be, for example, the electronic signal ES shown and described above that is sent to any of the ultrasonic energy delivery assemblies shown and described above (e.g., ultrasonic energy delivery assembly 105). The ultrasonic energy delivery assembly is characterized by a natural frequency, and the electronic signal is characterized by a frequency. As described above, the electronic signal can be produced and/or sent via an ultrasonic generator (that includes a control module and a feedback module) of the types shown and described herein.

At 504, a control signal is produced to randomly vary the frequency of the electronic signal within a range defined in part by the natural frequency of the ultrasonic energy delivery system and/or any of the components therein. In some embodiments, the control signal can be produced and/or sent to randomly vary the frequency of the electronic signal at a control signal interval of, for example, between approximately 10 milliseconds and approximately 300 milliseconds.

At 506, the frequency of the electronic signal is varied in response to the control signal. For example, in some embodiments, the control signal can be sent to a power module of the types shown and described herein, and the power module can vary the electronic signal produced and/or sent.

In some embodiments, the control signal can be produced (e.g., by a control module of the types shown herein) based in part on a random value. In some embodiments, the random value can be generated by, for example, a random value generator. In other embodiments, the random value is generated in part on the random electrical noise contained within a noise signal. For example, in some embodiments, the method optionally includes receiving a feedback signal that is associated with the electronic signal, 508. The feedback signal can be generated by a feedback module of the types described herein. As described above, the feedback module is configured to generate a feedback signal and a noise signal and send the feedback signal and the noise signal to the control module. As described above, the control signal is based in part on the feedback signal sent from the feedback module to the control module.

In some embodiments, the method optionally includes adjusting the value or calculation of the natural frequency of the ultrasonic energy delivery system based in part on the feedback signal, 510. As described above, in some embodiments, a feedback module is configured to produce a feedback signal and a noise signal, whereby the feedback signal is associated with a nominal component of the electronic signal produced by the power module, and the noise signal is based at least in part on a noise component of the electronic signal produced by the power module. As described above, in some embodiments, the natural frequency of the ultrasonic energy delivery system can be calculated to account for variations in the natural frequency of the transmission member due to part-to-part variation, and the conditions in which the energy delivery assembly is used, and the like.

In some embodiments, the method optionally includes adjusting the control signal based in part on a noise component of the feedback signal. 512. As described above, the control signal can be adjusted to allow for the generation of electronic signals of varying (random) frequency. This can result in random spatial variation in the vibrational nodes and anti-nodes along the length of the transmission member, which can lead to increased mechanical stability of the transmission member and reduce the likelihood of mechanical failure.

FIG. 13 is a flowchart illustrating a method of receiving a first and a second feedback signal and sending a control signal based in part on the feedback signals to vary the frequency of an electronic signal, according to an embodiment. The method 600 includes receiving a first feedback signal associated with a nominal component of an electronic signal conveyed to an ultrasonic energy delivery assembly that is characterized by a natural frequency, at 602. As described above, the first feedback signal can be generated by a feedback module that is operatively coupled to a control module of an ultrasonic generator.

At 604, the natural frequency of the ultrasonic energy delivery assembly is determined based at least in part on the first feedback signal sent by the feedback module to the control module. The natural frequency of the ultrasonic energy delivery system can be determined periodically to account for variations in the natural frequency of the transmission member due to part-to-part variation, and the conditions in which the ultrasonic energy delivery assembly is used such as, for example, the tortuous anatomic structures at sites of treatment.

At 606, a second feedback signal associated with a noise component of the electronic signal is received at the control module. As described above, the second feedback signal contains information associated with the random noise present in the electronic signal that is generated by the power module. The random noise can include, for example, thermal noise, shot noise, flicker noise, burst noise, avalanche noise, and/or the like.

At 608, a control signal based at least in part on the second feedback signal is sent to vary the frequency of the electronic signal. As described above, the noise component of the electronic signal is used to introduce random changes in the frequency of the electronic signal. This change in frequency is within a range determined by the fluctuations in random noise associated with the electronic signal and is about the natural frequency of the ultrasonic energy delivery assembly.

FIG. 14 is a flowchart illustrating a method of sending an electronic signal characterized by a frequency in response to receiving a control signal based in part on a random value, according to an embodiment. The method 700 includes sending an electronic signal from, for example, a power module, which is to be received by an ultrasonic energy delivery assembly characterized by a natural frequency, at 702. Additionally, the electronic signal is also characterized by a frequency which can be randomly varied by, for example, the power module, based on the contents of the control signal, as described herein.

At 704, a control signal is received by, for example, the power module where the control signal is based in part on a random value. As described above, in some configurations, the random value can be generated by a hardware or software random (or pseudo-random) value generator in the control module. In other configurations, the random value can be based at least in part on the (random) noise component of the electronic signal that is sent from the power module. As described above, the random noise present in electronic signals can include (but is not limited to), for example, thermal noise, shot noise, flicker noise, burst noise, avalanche noise, and/or the like.

At 706, the frequency of the electronic signal is varied by, for example, the power module, and is varied within a range defined at least in part by the natural frequency of the ultrasonic energy delivery assembly in response to receiving the control signal. As described above, the frequency of the electronic signal is varied within a range determined by the fluctuations in (random) noise associated with the electronic signal and is about the natural frequency of the ultrasonic energy delivery assembly. This change in frequency of the electronic signal can lead to standing waves where the locations of the vibrational nodes and anti-nodes along the length of the transmission member are non-permanent. Hence, this can lead to increased mechanical stability and reduced likelihood of mechanical failure.

Any of the ultrasonic generators and/or modules described herein can include any suitable processor such that the generator and/or module performs the functions described herein. Such processors can be a general-purpose processor (e.g., a central processing unit (CPU)) or other processor configured to execute one or more instructions stored in the memory. In some embodiments, the processor can alternatively be an application-specific integrated circuit (ASIC) or a field programmable gate array (FPGA). The processor can be configured to execute specific modules and/or sub-modules that can be, for example, hardware modules, software modules stored in the memory and executed in the processor, and/or any combination thereof. The memory included in the ultrasonic generator 180 or any of the ultrasonic generators disclosed herein can be, for example, flash memory, one time programmable memory, a random access memory (RAM), a memory buffer, a hard drive, a read-only memory (ROM), an erasable programmable read-only memory (EPROM), and/or so forth. In some embodiments, the memory includes a set of instructions to cause the processor to execute modules, processes and/or functions used to generate, control, amplify, and/or transfer electric current to another portion of the system, for example, the transducer assembly 150.

Some embodiments described herein relate to a computer storage product with a non-transitory computer-readable medium (also can be referred to as a non-transitory processor-readable medium) having instructions or computer code thereon for performing various computer-implemented operations. The computer-readable medium (or processor-readable medium) is non-transitory in the sense that it does not include transitory propagating signals per se (e.g., a propagating electromagnetic wave carrying information on a transmission medium such as space or a cable). The media and computer code (also can be referred to as code) may be those designed and constructed for the specific purpose or purposes. Examples of non-transitory computer-readable media include, but are not limited to: magnetic storage media such as hard disks, floppy disks, and magnetic tape; optical storage media such as Compact Disc/Digital Video Discs (CD/DVDs), Compact Disc-Read Only Memories (CD-ROMs), and holographic devices; magneto-optical storage media such as optical disks; carrier wave signal processing modules; and hardware devices that are specially configured to store and execute program code, such as Application-Specific Integrated Circuits (ASICs), Programmable Logic Devices (PLDs), Read-Only Memory (ROM) and Random-Access Memory (RAM) devices. Other embodiments described herein relate to a computer program product, which can include, for example, the instructions and/or computer code discussed herein.

Examples of computer code include, but are not limited to, micro-code or micro-instructions, machine instructions, such as produced by a compiler, code used to produce a web service, and files containing higher-level instructions that are executed by a computer using an interpreter. For example, embodiments may be implemented using assembly language, Java, C++, or other programming languages (e.g., object-oriented programming languages) or combined two languages (e.g. C++ and assembly language), and development tools. Additional examples of computer code include, but are not limited to, control signals, encrypted code, and compressed code.

While various embodiments have been described above, it should be understood that they have been presented by way of example only, and not limitation. Where methods and/or schematics described above indicate certain events and/or flow patterns occurring in certain order, the ordering of certain events and/or flow patterns may be modified. Additionally certain events may be performed concurrently in parallel processes when possible, as well as performed sequentially. While the embodiments have been particularly shown and described, it will be understood that various changes in form and details may be made.

For example, although described as sending an electronic signal ES that is substantially continuous, in other embodiments, any of the systems and methods described herein can include sending a series of discrete electronic signals. Said another way, in some embodiments, any of the systems and methods described herein can include sending a pulsed signal, which produces a pulsed ultrasonic energy signal. For example, in some embodiments, the methods and apparatus described herein can produce a first ultrasonic signal generated by a transducer assembly (e.g., transducer assembly 150) as a result of a first electrical signal sent from an ultrasonic generator (e.g., ultrasonic generator 180). The first electrical signal can be sent to the transducer assembly at a first time. A second ultrasonic signal can be generated by the transducer assembly as a result of a second electrical signal sent from the ultrasonic generator at a second time. In particular, in some embodiments, the frequency of the second ultrasonic signal is randomly varied from the frequency of the first ultrasonic signal within a range defined at least in part by the natural frequency of the ultrasonic energy delivery assembly.

Although some embodiments are described herein as sending a control signal to a power module that randomly varies the frequency of an ultrasonic electronic signal and/or an ultrasonic energy signal, in other embodiments, any of the devices, systems and methods described herein can be used to randomly vary any suitable parameter associated with the operation of an ultrasonic energy delivery system. For example, in some embodiments, an ultrasonic generator can include a control module and a feedback module. The feedback module is configured to produce a noise signal, as shown and described herein. The control module can produce and/or send a control signal to a portion of a delivery system (e.g., a power module) that is based on the noise signal. In response to the control signal, the portion of the delivery system can then vary a pulse interval between electronic signals, an amplitude of an electronic signal, a phase of an electronic signal or the like. In this manner, the feedback circuit can employ the noise signal to change the operating characteristics of the ultrasonic energy delivery system.

Although various embodiments have been described as having particular features and/or combinations of components, other embodiments are possible having a combination of any features and/or components from any of embodiments where appropriate. For example, any of the embodiments described herein can include a feedback module 383, a feedback module 483 or a feedback module 583 as shown and described above.

What is claimed is:
1. An apparatus, comprising:
a generator including a control module and a feedback module, the feedback module operatively coupled to the control module, the generator operably coupled to a power module configured to produce an electronic signal to be received by an ultrasonic energy delivery assembly that is characterized by a natural frequency, the electronic signal characterized by a frequency, the feedback module configured to produce a feedback signal, the feedback signal associated with a nominal component of the electronic signal produced by the power module,
the control module configured to receive a noise signal associated with a noise component of the electronic signal produced by the power module, the control module configured to determine the natural frequency based on the feedback signal, the control module configured to send a control signal, based at least in part on the noise signal, to the power module to randomly vary the frequency of the electronic signal within a range defined at least in part by the natural frequency.

2. The apparatus of claim 1, wherein the control module is configured to send the control signal as a function of time.

3. The apparatus of claim 1, wherein the control module is configured to send the control signal at a control signal interval of between approximately 10 milliseconds and approximately 300 milliseconds.

4. The apparatus of claim 1, wherein the control module is configured to produce a random value, the control signal based at least in part on the random value.

5. The apparatus of claim 1, wherein the generator includes a noise detection module operatively coupled to the control module, the noise detection module configured to produce the noise signal associated with the noise component of the electronic signal produced by the power module.

6. The apparatus of claim 1, wherein the generator includes a noise detection module operatively coupled to the control module, the noise detection module implemented at least in part in hardware, the noise detection module including at least one of a sensor, an amplifier, a filter or an analog to digital converter, the noise detection module configured to produce the noise signal associated with the noise component of the electronic signal produced by the power module.

7. The apparatus of claim 1, wherein the control module is configured to vary the range within which the frequency of the electronic signal is varied.

8. The apparatus of claim 1, wherein the control signal is associated with a frequency set point.

9. The apparatus of claim 1, wherein the feedback module is implemented at least in part in hardware, the feedback module including at least one of a sensor, an amplifier, a filter or an analog to digital converter, the feedback module configured to produce the noise signal.

10. The apparatus of claim 1, wherein the feedback module is implemented at least in part in hardware and includes a sensor and a filter, the sensor configured to detect at least one of a current or a voltage of the electronic signal, the filter configured to limit a detection frequency range of the electronic signal, the feedback module configured to produce the noise signal.

11. The apparatus of claim 1, wherein:
the feedback module is implemented at least in part in hardware and includes a sensor and a filter, the sensor configured to detect at least one of a current or a voltage of the electronic signal, the feedback module configured to produce the noise signal; and
the control module includes a processor configured to generate the control signal based on the natural frequency, the noise signal, and the range.

12. An apparatus, comprising:
a generator including a control module and a feedback module, the feedback module operatively coupled to the control module, the generator operably coupled to a power module configured to produce an electronic signal to be received by an ultrasonic energy delivery assembly that is characterized by a natural frequency, the electronic signal characterized by a frequency, the feedback module configured to produce a feedback signal, the feedback signal associated with a nominal component of the electronic signal produced by the power module, the control module configured to determine the natural frequency based on the feedback signal, the control module including a random number generator configured to produce a random value, the control module configured to generate a control signal based at least in part on the random value and send the control signal to the power module to randomly vary the frequency of the electronic signal within a range defined at least in part by the natural frequency.

13. The apparatus of claim 12, wherein the control module includes a processor configured to implement a random number generator to produce the random value.

14. The apparatus of claim 12, wherein the feedback module is implemented at least in part in hardware and includes a sensor and a filter, the sensor configured to detect at least one of a current or a voltage of the electronic signal, the filter configured to limit a detection frequency range of the electronic signal.

15. The apparatus of claim 12, wherein:
the feedback module is implemented at least in part in hardware and includes a sensor and a filter, the sensor configured to detect at least one of a current or a voltage of the electronic signal; and the control module includes a processor configured to generate the control signal based on the natural frequency, the random value, and the range.

16. The apparatus of claim 12, wherein the control module is configured to send the control signal as a function of time.

17. The apparatus of claim 12, wherein the control module is configured to send the control signal at a control signal interval of between approximately 10 milliseconds and approximately 300 milliseconds.

18. The apparatus of claim 12, wherein:
the feedback module is implemented at least in part in hardware and includes a sensor and a filter, the sensor configured to detect at least one of a current or a voltage of the electronic signal, the feedback module configured to produce a noise signal associated with a noise component of the electronic signal produced by the power module; and the control module is configured to receive the noise signal, the random number generator being implemented in a processor and configured to produce the random value based at least in part on the noise signal.

19. The apparatus of claim 12, wherein the control module is configured to vary the range within which the frequency of the electronic signal is varied.

20. The apparatus of claim 12, wherein the control signal is associated with a frequency set point.

21. The apparatus of claim 12, wherein the control module is configured to determine the natural frequency at a first time, the control module configured to send the control signal at a second time after the first time.

* * * * *